United States Patent
Hirai et al.

(10) Patent No.: US 12,187,821 B2
(45) Date of Patent: Jan. 7, 2025

(54) FLUOROSULFONYL GROUP-CONTAINING COMPOUND, FLUOROSULFONYL GROUP-CONTAINING MONOMER, AND THEIR PRODUCTION METHODS

(71) Applicant: AGC Inc., Tokyo (JP)

(72) Inventors: Takeshi Hirai, Tokyo (JP); Daisuke Jomuta, Tokyo (JP); Chikaya Tamitsuji, Tokyo (JP)

(73) Assignee: AGC Inc., Tokyo (JP)

( * ) Notice: Subject to any disclaimer, the term of this patent is extended or adjusted under 35 U.S.C. 154(b) by 612 days.

(21) Appl. No.: 17/505,679

(22) Filed: Oct. 20, 2021

(65) Prior Publication Data

US 2022/0041765 A1 Feb. 10, 2022

Related U.S. Application Data

(60) Division of application No. 16/801,222, filed on Feb. 26, 2020, now Pat. No. 11,242,420, which is a continuation of application No. PCT/JP2018/032433, filed on Aug. 31, 2018.

(30) Foreign Application Priority Data

Sep. 1, 2017 (JP) .................. 2017-168659
May 10, 2018 (JP) .................. 2018-091756
May 10, 2018 (JP) .................. 2018-091757

(51) Int. Cl.
*C08F 214/26* (2006.01)
*B01D 67/00* (2006.01)
*B01D 69/02* (2006.01)
*B01D 71/32* (2006.01)
*B01D 71/36* (2006.01)
(Continued)

(52) U.S. Cl.
CPC .......... *C08F 14/26* (2013.01); *B01D 67/0093* (2013.01); *B01D 69/02* (2013.01); *B01D 71/32* (2013.01); *B01D 71/36* (2013.01); *B01D 71/82* (2013.01); *B01J 39/20* (2013.01); *C07C 303/22* (2013.01); *C07C 309/80* (2013.01); *C07C 309/82* (2013.01); *C08F 8/12* (2013.01); *C08F 16/24* (2013.01); *C08F 16/30* (2013.01); *C08F 214/26* (2013.01); *C08F 214/262* (2013.01); *C08F 216/1475* (2020.02); *C08J 5/2237* (2013.01); *C08J 5/225* (2013.01); *C08L 27/22* (2013.01); *C25B 1/02* (2013.01); *C25B 1/04* (2013.01); *C25B 1/46* (2013.01); *C25B 13/08* (2013.01); *H01B 1/122* (2013.01); *H01M 4/8663* (2013.01); *H01M 8/10* (2013.01); *H01M 8/1004* (2013.01); *H01M 8/1007* (2016.02); *H01M 8/1023* (2013.01); *H01M 8/1039* (2013.01); *H01M 8/188* (2013.01); *H01M 10/0565* (2013.01); *H01M 50/411* (2021.01); *B01D 69/145* (2013.01); *B01D 2325/04* (2013.01); *B01D 2325/14* (2013.01); *B01D 2325/42* (2013.01); *H01M 2008/1095* (2013.01); *H01M 2300/0082* (2013.01); *Y02E 60/10* (2013.01); *Y02E 60/36* (2013.01); *Y02E 60/50* (2013.01); *Y02P 70/50* (2015.11)

(58) Field of Classification Search
None
See application file for complete search history.

(56) References Cited

U.S. PATENT DOCUMENTS 3,282,875 A * 11/1966 Connolly .............. C07C 309/82
562/110
8,097,383 B2 1/2012 Kaneko et al.
(Continued)

FOREIGN PATENT DOCUMENTS

EP 1 640 362 A2 3/2006
JP 2004-143055 A 5/2004
(Continued)

OTHER PUBLICATIONS

Extended European Search Report issued May 17, 2021 in European Patent Application No. 18850471.6, 7 pages.
(Continued)

*Primary Examiner* — David J Buttner
(74) *Attorney, Agent, or Firm* — Oblon, McClelland, Maier & Neustadt, L.L.P.

(57) ABSTRACT

A method for producing a fluorosulfonyl group-containing compound to obtain a compound represented by the following formula 5 from a compound represented by the following formula 1 as a starting material and a method for producing a fluorosulfonyl group-containing monomer in which the fluorosulfonyl group-containing compound is used:

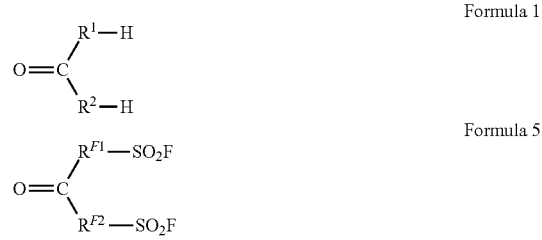

wherein $R^1$ and $R^2$ are a $C_{1-3}$ alkylene group, and $R^{F1}$ and $R^{F2}$ are a $C_{1-3}$ perfluoroalkylene group.

4 Claims, No Drawings

(51) Int. Cl.

| | |
|---|---|
| *B01D 71/82* | (2006.01) |
| *B01J 39/20* | (2006.01) |
| *C07C 303/22* | (2006.01) |
| *C07C 309/80* | (2006.01) |
| *C07C 309/82* | (2006.01) |
| *C08F 8/12* | (2006.01) |
| *C08F 14/26* | (2006.01) |
| *C08F 16/24* | (2006.01) |
| *C08F 16/30* | (2006.01) |
| *C08F 216/14* | (2006.01) |
| *C08J 5/22* | (2006.01) |
| *C08L 27/22* | (2006.01) |
| *C25B 1/02* | (2006.01) |
| *C25B 1/04* | (2021.01) |
| *C25B 1/46* | (2006.01) |
| *C25B 13/08* | (2006.01) |
| *H01B 1/12* | (2006.01) |
| *H01M 4/86* | (2006.01) |
| *H01M 8/10* | (2016.01) |
| *H01M 8/1004* | (2016.01) |
| *H01M 8/1007* | (2016.01) |
| *H01M 8/1023* | (2016.01) |
| *H01M 8/1039* | (2016.01) |
| *H01M 8/18* | (2006.01) |
| *H01M 10/0565* | (2010.01) |
| *H01M 50/411* | (2021.01) |
| *B01D 69/14* | (2006.01) |

(56) References Cited

U.S. PATENT DOCUMENTS

| | | |
|---|---|---|
| 2006/0106252 A1 | 5/2006 | Murata et al. |
| 2016/0347966 A1 | 12/2016 | Dadalas et al. |

FOREIGN PATENT DOCUMENTS

| | | |
|---|---|---|
| JP | 2011-241344 A | 12/2011 |
| WO | WO 2005/003062 A2 | 1/2005 |
| WO | WO 2007/013532 A1 | 2/2007 |
| WO | WO 2007/013533 A1 | 2/2007 |
| WO | WO 2011/144992 A1 | 11/2011 |

OTHER PUBLICATIONS

Ermolov, A.F., et al., "Acylation of tertiary fluorocarbanions", Zhurnal Organicheskoi Khimii, Maik Nauka, Moscow, Russia, col. 19, No. 6, Jan. 1, 1983, XP009526828, pp. 1343, 1344.
Brouwer, D.M., et al., "Reactions of Hydroxycarbonium Ion in Strong Acids IV*", Recueil (1971), 2010, pp. 1010-1026.
International Search Report issued Oct. 30, 2018 in PCT/JP2018/032433 filed Aug. 31, 2018, 2 pages.
On-line reference, "Ion-Exchange Membranes", https://xumuk.ru/encyklopedia/2504.html, Chemical Encyclopedia, Kozhevnikova NE, Nefedova G. 3, (1975) (with Machine English Translation).
Fumio Ogura et al., "Dimethyl and Diethyl 2-Oxo-1,3-propanedisulfonates as Practical Alkylating Reagents," *Bull. Chem. Soc. Japan*, (vol. 56) No. 4, 1257-1258 (1983).

* cited by examiner

FLUOROSULFONYL GROUP-CONTAINING COMPOUND, FLUOROSULFONYL GROUP-CONTAINING MONOMER, AND THEIR PRODUCTION METHODS

CROSS REFERENCE TO RELATED APPLICATIONS

This application is a divisional application of prior U.S. application Ser. No. 16/801,222 filed Feb. 26, 2020, the disclosure of which is incorporated herein by reference in its entirety. U.S. application Ser. No. 16/801,222 now U.S. Pat. No. 11,242,420 is a continuation application of PCT JP2018/032433, filed Aug. 31, 2018, the disclosure of which is incorporated herein by reference in its entirety. U.S. application Ser. No. 16/801,222 claims priority to Japanese Application No. 2017-168659, filed Sep. 1, 2017, Japanese Application No. 2018-091756, filed May 10, 2018, and Japanese Application No. 2018-091757, filed May 10, 2018, the disclosures of which are incorporated herein by reference in their entireties.

TECHNICAL FIELD

The present invention relates to a fluorosulfonyl group-containing compound, a fluorosulfonyl group-containing monomer and their production methods.

BACKGROUND ART

A polymer contained in a catalyst layer or a polymer electrolyte membrane in a membrane/electrode assembly for a polymer electrolyte fuel cell, a cation exchange membrane to be used for alkali chloride electrolysis, etc. is desired to have a high ion exchange capacity. When the ion exchange capacity is high, the ion conductivity improves, and accordingly, for example, practical advantages are expected, such as an improvement of power generation performance of a polymer electrolyte fuel cell and a reduction of the electric power consumption rate by a reduction of overvoltage of a membrane resistance or the like in alkali chloride electrolysis.

As a polymer having a high ion exchange capacity, a sulfonic acid group-containing polymer formed by converting fluorosulfonyl groups in a fluorosulfonyl group-containing polymer having units based on a monomer having two fluorosulfonyl groups in one molecule and units based on tetrafluoroethylene, into sulfonic acid groups, has been proposed (Patent Documents 1 to 3).

PRIOR ART DOCUMENTS

Patent Documents

Patent Document 1: WO2005/003062
Patent Document 2: WO2007/013532
Patent Document 3: WO2007/013533

DISCLOSURE OF INVENTION

Technical Problem

However, in the production of a monomer having two fluorosulfonyl groups in one molecule, there are problems such that some starting material compounds are expensive, the yield of the monomer to be finally obtained is low on the starting material basis, and many synthetic steps are included. For example, in preparation of monomers having two fluorosulfonyl groups in one molecule by using benzyl mercaptan and epichlorohydrin as starting materials as disclosed in Ex. 2 to Ex. 4 in Patent Document 1, the reaction yield on the starting material basis in all steps for synthesizing monomers is low at a level of 2%, and a large amount of starting materials and a reaction agent are thereby required. For such a reason, conventional monomers having two fluorosulfonyl groups in one molecule are expensive.

The present invention provides a method for producing a fluorosulfonyl group-containing compound, whereby a fluorosulfonyl group-containing compound which is useful as an intermediate for a monomer having two fluorosulfonyl groups in one molecule can be produced at a low cost by a few synthetic steps.

Further, the present invention provides a method for producing a fluorosulfonyl group-containing monomer, whereby a monomer having two fluorosulfonyl groups in one molecule can be produced at a low cost by a few synthetic steps.

Further, the present invention provides a fluorosulfonyl group-containing compound which is useful as an intermediate for a monomer having two fluorosulfonyl groups in one molecule.

Further, the present invention provides a fluorosulfonyl group-containing monomer having two fluorosulfonyl groups in one molecule which is inexpensive as compared with conventional one.

Solution to Problem

The present invention has the following features.

[1] A method for producing a fluorosulfonyl group-containing compound, which comprises:
reacting a compound represented by the following formula 1 with a sulfonating agent to obtain a compound represented by the following formula 2,
reacting the compound represented by the following formula 2 with a chlorinating agent to obtain a compound represented by the following formula 3,
reacting the compound represented by the following formula 3 with a fluorinating agent to obtain a compound represented by the following formula 4, and
subjecting the compound represented by the following formula 4 to fluorination treatment to obtain a compound represented by the following formula 5:

Formula 1

$$O=C\begin{matrix}R^1-H\\ \\R^2-H\end{matrix}$$

Formula 2

Formula 3

Formula 4

Formula 5

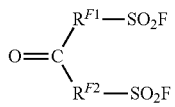

wherein $R^1$ and $R^2$ are a $C_{1-3}$ alkylene group, and $R^{F1}$ and $R^{F2}$ are a $C_{1-3}$ perfluoroalkylene group.

[2] A method for producing a fluorosulfonyl group-containing monomer, which comprises:

obtaining the compound represented by the formula 5 by the method for producing a fluorosulfonyl group-containing compound as defined in the above [1], and reacting the compound represented by the formula 5 with a perfluoroallylating agent to obtain a compound represented by the following formula 7:

Formula 7

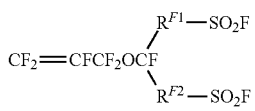

wherein $R^{F1}$ and $R^{F2}$ are a $C_{1-3}$ perfluoroalkylene group.

[3] A method for producing a fluorosulfonyl group-containing monomer, which comprises:

obtaining the compound represented by the formula 5 by the method for producing a fluorosulfonyl group-containing compound as defined in the above [1], adding 2 moles of hexafluoropropylene oxide to 1 mole of the compound represented by the formula 5 in the presence of a metal fluoride to obtain a compound represented by the following formula 8a, and thermally decomposing the compound represented by the following formula 8a to obtain a compound represented by the following formula 9a:

Formula 8a

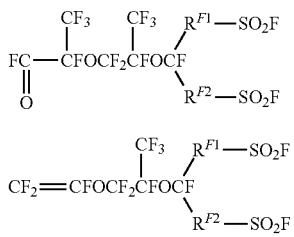

Formula 9a wherein $R^{F1}$ and $R^{F2}$ are a $C_{1-3}$ perfluoroalkylene group.

[4] A method for producing a fluorosulfonyl group-containing monomer, which comprises obtaining the compound represented by the formula 5 by the method for producing a fluorosulfonyl group-containing compound as defined in the above [1], adding 1 mole of hexafluoropropylene oxide to 1 mole of the compound represented by the formula 5 in the presence of a metal fluoride to obtain a compound represented by the following formula 8b, and thermally decomposing the compound represented by the following formula 8b to obtain a compound represented by the following formula 10:

Formula 8b

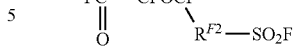
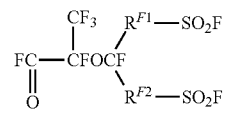

Formula 10

wherein $R^{F1}$ and $R^{F2}$ are a $C_{1-3}$ perfluoroalkylene group.

[5] A method for producing a fluorosulfonyl group-containing monomer, which comprises reacting a compound represented by the following formula 5 with a perfluoroallylating agent to obtain a compound represented by the following formula 7:

Formula 5

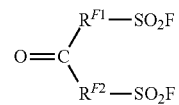

Formula 7

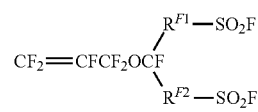

wherein $R^{F1}$ and $R^{F2}$ are a $C_{1-3}$ perfluoroalkylene group.

[6] A method for producing a fluorosulfonyl group-containing monomer, which comprises adding 2 moles of hexafluoropropylene oxide to 1 mole of a compound represented by the following formula 5 in the presence of a metal fluoride to obtain a compound represented by the following formula 8a, and thermally decomposing the compound represented by the following formula 8a to obtain a compound represented by the following formula 9a:

Formula 5

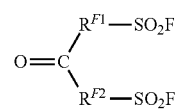

Formula 8a

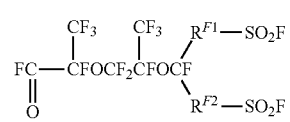

Formula 9a

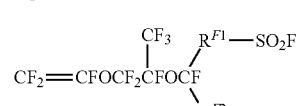

wherein $R^{F1}$ and $R^{F2}$ are a $C_{1-3}$ perfluoroalkylene group.

[7] A method for producing a fluorosulfonyl group-containing monomer, which comprises adding 1 mole of hexafluoropropylene oxide to 1 mole of a compound represented by the following formula 5 in the presence of a metal fluoride to obtain a compound represented by the following formula 8b, and thermally decomposing the compound represented by the following formula 8b to obtain a compound represented by the following formula 10:

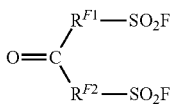

Formula 5

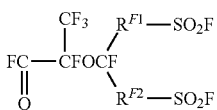

Formula 8b

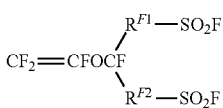

Formula 10 wherein $R^{F1}$ and $R^{F2}$ are a $C_{1-3}$ perfluoroalkylene group.

[8] A fluorosulfonyl group-containing compound, which is a compound represented by the following formula 4:

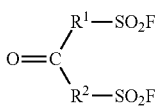

Formula 4 wherein $R^1$ and $R^2$ are a $C_{1-3}$ alkylene group.

[9] A fluorosulfonyl group-containing compound, which is either one or both of a compound represented by the following formula 5 and a compound represented by the following formula 5':

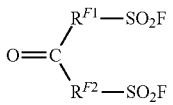

Formula 5

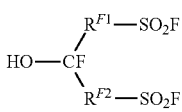

Formula 5' wherein $R^{F1}$ and $R^{F2}$ are a $C_{1-3}$ perfluoroalkylene group.

[10] A fluorosulfonyl group-containing monomer, which is a compound represented by the following formula 7:

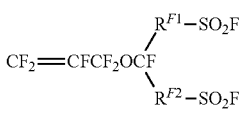

Formula 7 wherein $R^{F1}$ and $R^{F2}$ are a $C_{1-3}$ perfluoroalkylene group.

[11] A fluorosulfonyl group-containing monomer, which is a compound represented by the following formula 9a:

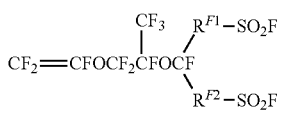

Formula 9a wherein $R^{F1}$ and $R^{F2}$ are a $C_{1-3}$ perfluoroalkylene group.

[12] A fluorosulfonyl group-containing monomer, which is a compound represented by the following formula 10:

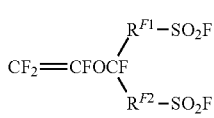

Formula 10 wherein $R^{F1}$ and $R^{F2}$ are a $C_{1-3}$ perfluoroalkylene group.

Advantageous Effects of Invention

According to the method for producing a fluorosulfonyl group-containing compound of the present invention, a fluorosulfonyl group-containing compound which is useful as an intermediate for a fluorosulfonyl group-containing monomer can be produced at a low cost by a few synthetic steps.

According to the method for producing a fluorosulfonyl group-containing monomer of the present invention, a monomer having two fluorosulfonyl groups in one molecule can be produced at a low cost by a few steps.

The fluorosulfonyl group-containing compound of the present invention is useful as an intermediate for a fluorosulfonyl group-containing monomer. Various fluorosulfonyl group-containing monomers can be produced from the fluorosulfonyl group-containing compound of the present invention.

The fluorosulfonyl group-containing monomer of the present invention has two fluorosulfonyl groups in one molecule and is inexpensive as compared with conventional one. Further, a membrane made of a polymer obtained by polymerizing the monomer has a high ion exchange capacity and an excellent ion conductivity.

DESCRIPTION OF EMBODIMENTS

Definitions of Terms, Etc

The following definitions of terms and ways of expressions apply throughout the present specification and the scope of Claims.

A compound represented by the formula 1 is referred to as "compound 1". Compounds represented by other formulae are similarly referred.

Units represented by the formula u1 are referred to as "units u1". Structural units represented by other formulae are similarly referred.

"Units based on a monomer" is a collective term of an atomic group directly formed by polymerization of one molecule of a monomer and an atomic group obtained by chemically converting a part of the atomic group.

"Sulfonic acid group" is a collective term of a salt form sulfonic acid group ($-SO_3^-$ $M^+$ wherein $M^+$ is a metal ion or an ammonium ion) and an acid form sulfonic acid group ($-SO_3^-H^+$).

The expression "to" showing a numerical range is used to include the numerical values before and after it as the lower limit value and the upper limit value.

(Fluorosulfonyl Group-Containing Monomer)

The fluorosulfonyl group-containing monomer of the present invention according to a first embodiment is a compound 7.

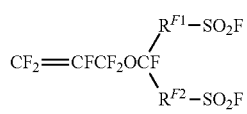

Formula 7

The fluorosulfonyl group-containing monomer of the present invention according to a second embodiment is a compound 9.

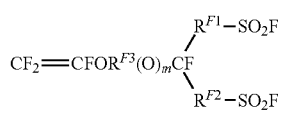

Formula 9

The fluorosulfonyl group-containing monomer of the present invention according to a third embodiment is a compound 10.

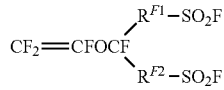

Formula 10

Here, $R^{F1}$ and $R^{F2}$ are a $C_{1-3}$ perfluoroalkylene group, $R^{F3}$ is a $C_{1-6}$ perfluoroalkylene group, and m is 0 or 1. $R^{F1}$ and $R^{F2}$ may be the same or different.

As $R^{F1}$ and $R^{F2}$, $-CF_2-$, $-CF_2CF_2-$, $-CF(CF_3)-$, $-CF_2CF_2CF_2-$, $-CF(CF_2CF_3)-$, $-CF(CF_3)CF_2-$, $-CF_2CF(CF_3)-$, $-C(CF_3)(CF_3)-$, etc. may be mentioned. $R^{F1}$ and $R^{F2}$ preferably have one or two carbon atoms and are preferably linear, whereby starting materials are more inexpensive, the production of the compound 7, the compound 9 or the compound 10 is easy, and a sulfonic acid group-containing polymer to be produced from a fluorosulfonyl group-containing monomer has a higher ion exchange capacity. Specifically, $-CF_2-$, $-CF_2CF_2-$ or $-CF(CF_3)-$ is preferred, and $-CF_2-$ is more preferred.

As $R^{F3}$, $-CF_2-$, $-CF_2CF_2-$, $-CF(CF_3)-$, $-CF_2CF_2CF_2-$, $-CF(CF_2CF_3)-$, $-CF(CF_3)CF_2-$, $-CF_2CF(CF_3)-$, $-C(CF_3)(CF_3)-$, $-CF_2CF(CF_3)OCF_2CF(CF_3)-$, etc. may be mentioned. $R^{F3}$ preferably has from one to three carbon atoms, whereby starting materials are more inexpensive, the production of the compound 9 is easy, and a sulfonic acid group-containing polymer to be produced from a fluorosulfonyl group-containing monomer has a higher ion exchange capacity. Specifically, $-CF_2-$, $-CF_2CF_2-$ or $-CF_2CF(CF_3)-$ is preferred, and $-CF_2CF(CF_3)-$ is more preferred.

The compound 7 may, for example, be compound 7-1.

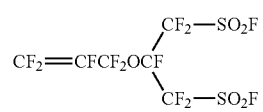

Formula 7-1

The compound 9 may, for example, be compound 9-1, compound 9-2 or compound 9-3.

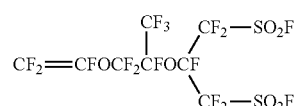

Formula 9-1

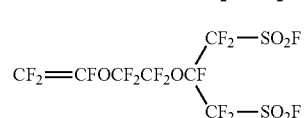

Formula 9-2

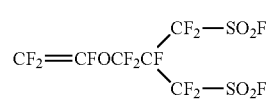

Formula 9-3

The compound 10 may, for example, be compound 10-1.

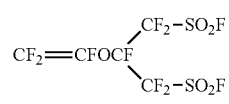

Formula 10-1

As the fluorosulfonyl group-containing compound which is useful as an intermediate for the compound 7, the compound 9 or the compound 10, the compound 4 or either one or both of the compound 5 and the compound 5' may be mentioned. In the presence of hydrogen fluoride (HF), hydrogen fluoride is added to the compound 5, and the compound 5 is thereby in equilibrium state with the compound 5' (alcohol), or the compound 5 becomes the compound 5' in some cases. In this specification, the compound 5 simply described may sometimes represent either one or both of the compound 5 and the compound 5'.

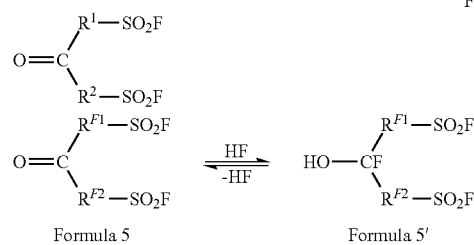

wherein $R^1$ and $R^2$ are a $C_{1-3}$ alkylene group. $R^1$ and $R^2$ may be the same or different.

As $R^1$ and $R^2$, $-CH_2-$, $-CH_2CH_2-$, $-CH(CH_3)-$, $-CH_2CH_2CH_2-$, $-CH(CH_2CH_3)-$, $-CH(CH_3)CH_2-$, $-CH_2CH(CH_3)-$, $-C(CH_3)(CH_3)-$, etc., may be mentioned. $R^1$ and $R^2$ preferably have one or two carbon atoms and are preferably linear, whereby the compound 1 as a starting material is further inexpensive, the production of the compound 5 is easy, and a sulfonic acid group-containing polymer to be produced from an intermediate has a higher ion exchange capacity. Specifically, —$CH_2$—, —$CH_2CH_2$— or —$CH(CH_3)$— is preferred, and —$CH_2$— is more preferred.

$R^{F1}$ and $R^{F2}$ are the same as $R^{F1}$ and $R^{F2}$ described for the compound 7, and preferred forms are also the same.

The compound 4 and the compound 5 may be produced as described below.

The compound 1 and a sulfonating agent are reacted to obtain a compound 2, the compound 2 and a chlorinating agent are reacted to obtain a compound 3, the compound 3 and a fluorinating agent are reacted to obtain a compound 4, and the compound 4 is subjected to fluorination treatment to obtain a compound 5. As described above, in the presence of hydrogen fluoride, the compound 5' may be contained in the final product in some cases.

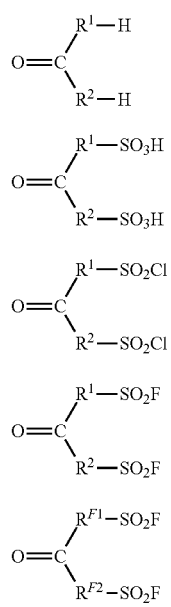

Formula 1

Formula 2

Formula 3

Formula 4

Formula 5

$R^1$ and $R^2$ are the same as $R^1$ and $R^2$ described for the compound 4, and preferred forms are also the same. Further, $R^{F1}$ and $R^{F2}$ are the same as $R^{F1}$ and $R^{F2}$ described for the compound 7, and preferred forms are also the same.

The compound 1 may, for example, be acetone, methyl ethyl ketone, diethyl ketone, methyl propyl ketone, ethyl propyl ketone, dipropyl ketone, diisopropyl ketone, isopropyl methyl ketone, isopropyl ethyl ketone or isopropyl propyl ketone. The compound 1 is preferably acetone, whereby the compound 1 is more inexpensive, the compound 7 can be easily produced, and the sulfonic acid group-containing polymer has a higher ion exchange capacity per unit molecular weight.

The sulfonating agent may, for example, be chlorosulfuric acid, fluorosulfonic acid, sulfur trioxide, a complex of sulfur trioxide, fuming sulfuric acid or concentrated sulfuric acid.

The reaction temperature of the compound 1 with a sulfonating agent is preferably from 0 to 100° C. The reaction solvent may be selected from solvents which are less likely to be sulfonated themselves. The reaction solvent may, for example, be methylene chloride, chloroform, carbon tetrachloride, 1,1,1-trichloromethane, cyclohexane, hexane, petroleum ether, pentane, heptane, diethyl ether or acetonitrile. Two or more of the reaction solvents may be used in combination.

The chlorinating agent may, for example, be thionyl chloride, phosphorus pentachloride, phosphorus trichloride, phosphoryl chloride, chlorosulfuric acid, sulfuryl chloride or oxalyl chloride.

The reaction temperature of the compound 2 with a chlorinating agent is preferably from 0 to 100° C. When the reaction temperature is at most the above upper limit value of the above range, the decomposition of the compound 3 is suppressed, whereby the yield of the compound 3 improves. When the reaction temperature is at least the lower limit value of the above range, the reaction rate increases, and the productivity thereby improves. Further, by using an agent having both functions of the sulfonating agent and the chlorinating agent such as chlorosulfuric acid, the sulfonation step and the chlorination step may be conducted at the same time.

The fluorinating agent may, for example, be potassium hydrogen fluoride, sodium hydrogen fluoride, potassium fluoride, sodium fluoride, cesium fluoride, silver fluoride, a quaternary ammonium fluoride (such as tetraethylammonium fluoride or tetrabutylammonium fluoride), hydrogen fluoride, hydrofluoric acid or a complex of hydrogen fluoride (such as a HF-pyridine complex or HF-triethylamine).

The reaction temperature of the compound 3 with a fluorinating agent is preferably from −30 to 100° C. The reaction solvent may be selected from polar solvents and low polar solvents which are less likely to be fluorinated. The reaction solvent may, for example, be methylene chloride, chloroform, carbon tetrachloride, 1,1,1-trichloromethane, diethyl ether, dioxane, tetrahydrofuran, dimethoxyethane, diethylene glycol dimethyl ether, tetraethylene glycol dimethyl ether, dimethylsulfoxide, sulfolane, N,N-dimethylformamide, acetonitrile, dimethyl carbonate, diethyl carbonate, ethylene carbonate, propylene carbonate or water. Two or more of the reaction solvents may be used in combination.

The fluorination treatment is carried out by bringing the compound 4 into contact with fluorine gas or a fluorine compound.

The fluorine compound may, for example, be hydrogen fluoride, a halogen fluoride (such as chlorine trifluoride or iodine pentafluoride), a gaseous fluoride (such as boron trifluoride, nitrogen trifluoride, phosphorus pentafluoride, silicon tetrafluoride or sulfur hexafluoride), a metal fluoride (such as lithium fluoride or nickel(II) fluoride), a hypofluorite compound (such as trifluoromethyl hypofluorite or trifluoroacetyl hypofluorite), an electrophilic fluorination reaction agent (Selectfluor (trade name) or N-fluorobenzene sulfonimide).

The fluorination treatment is preferably treatment of bringing the compound 4 into contact with fluorine gas, whereby handling is easy, and impurities to be contained in the compound 5 can be reduced. Fluorine gas may be diluted with an inert gas such as nitrogen gas. The temperature of the fluorination treatment is preferably from −20 to 350° C. The reaction solvent may be selected from solvents in which solubility of the compound 4 or the compound 5 is high and which are less likely to be susceptible to fluorination treatment themselves. The reaction solvent may, for example, be acetonitrile, chloroform, dichloromethane, trichloromethane, a perfluorotrialkylamine (such as perfluorotributylamine), a perfluorocarbon (such as perfluorohexane or perfluorooctane), a hydrofluorocarbon (such as 1H,4H- perfluorobutane or 1H-perfluorohexane), a hydrochlorofluorocarbon (such as 3,3-dichloro-1,1,1,2,2-pentafluoropropane or 1,3-dichloro-1,1,2,2,3-pentafluoropropane) or a hydrofluoroether (such as $CF_3CH_2OCF_2CF_2H$). In the fluorination with fluorine gas, hydrogen fluoride forms as a by-product together with the compound 5 as a product. Thus, the product may be in an equilibrium state of the compound 5 and the compound 5' or may become the compound 5' in some cases. Such a state varies depending on the existing amount of hydrogen fluoride, the temperature, the solvent, etc.

The compound 7 is produced by reacting the compound 5 with a perfluoroallylating agent. The perfluoroallylating agent may, for example, be a compound 6.

$CF_2\!=\!CFCF_2\text{-}G$      Formula 6 wherein G is $-OSO_2F$, $-OSO_2R^{f2}$, a chlorine atom, a bromine atom or an iodine atom, and $R^{f2}$ is a $C_{1-8}$ perfluoroalkyl group.

The compound 6 is preferably compound 6-1 from the viewpoint of availability of starting materials, the reactivity of the perfluoroallylating agent, the simplicity of synthesis and the handling efficiency.

$CF_2\!=\!CFCF_2OSO_2F$      Formula 6-1

For example, the compound 6-1 may be produced by reacting hexafluoropropylene and sulfur trioxide in the presence of boron trifluoride. A Lewis acid such as a boron trifluoride diethyl ether complex or trimethoxyborane may also be used instead of boron trifluoride.

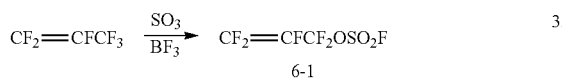

The reaction of the compound 5 with a perfluoroallylating agent is preferably carried out in the presence of a fluoride salt. The fluoride salt may, for example, be potassium fluoride, cesium fluoride, silver fluoride, quaternary ammonium fluoride or sodium fluoride.

The reaction temperature of the compound 5 with a perfluoroallylating agent is preferably from −70 to 40° C. The reaction solvent preferably contains an aprotic polar solvent and more preferably consists of an aprotic polar solvent only. The aprotic polar solvent may, for example, be monoglyme, diglyme, triglyme, tetraglyme, acetonitrile, propionitrile, adiponitrile, benzonitrile, dioxane, tetrahydrofuran, N,N-dimethylformamide, dimethylsulfoxide, N-methylpyrrolidone or nitroethane. Two or more of the reaction solvents may be used in combination. Further, as described above, in the presence of hydrogen fluoride, the compound 5 may be in an equilibrium state of the compound 5 and the compound 5' or may become the compound 5' in some cases. However, the reaction with an allylating agent or other reactions described below may be carried out in a state where the compound 5' is contained, since both compounds are in the relation of equilibrium.

Among the compound 9, a compound 9a such as the compound 9-1 can be produced by adding 2 moles of hexafluoropropylene oxide to 1 mole of the compound 5 in the presence of a catalytic amount of a metal fluoride (such as potassium fluoride or cesium fluoride) to obtain a compound 8a and thermally decomposing the compound 8a.

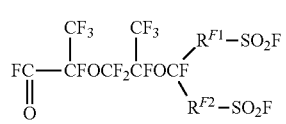
                  Formula 8a

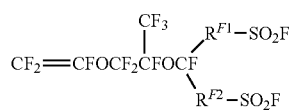
                  Formula 9a

Among the compound 9, the compound 9-2 can be produced as follows. 1 mole of the compound 5-1 is reacted with an equivalent amount of a metal fluoride, tetrafluoroethylene and iodine to obtain compound 8-2. The compound 8-2 is reacted with fuming sulfuric acid to obtain compound 8-3. 1 mole of hexafluoropropylene oxide is added to 1 mole of the compound 8-3 in the presence of a catalytic amount of a metal fluoride to obtain compound 8-4, and the compound 8-4 is thermally decomposed.

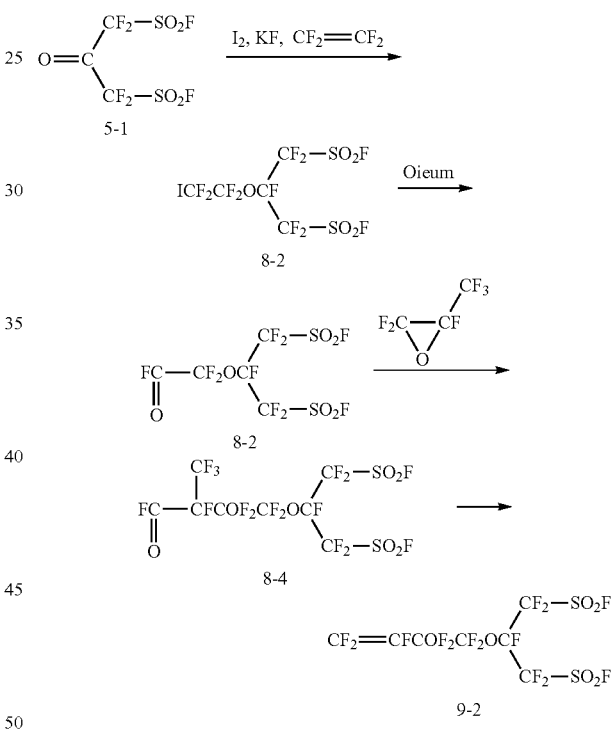

Among the compound 9, the compound 9-3 can be produced as follows. 1 mole of the compound 5-1 is reacted with 1 mole of a difluorocarbene generator such as hexafluoropropylene oxide to obtain compound 8-5. 1 mole of hexafluoropropylene oxide is added to 1 mole of the compound 8-5 in the presence of a catalytic amount of a metal fluoride to obtain compound 8-6, and the compound 8-6 is thermally decomposed.

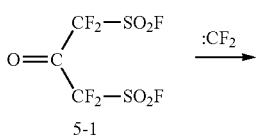

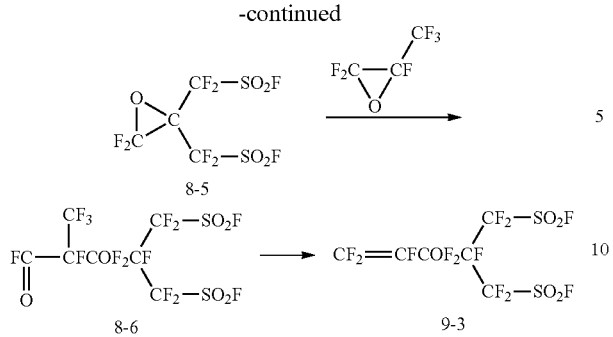

The compound 10 can be produced by adding 1 mole of hexafluoropropylene oxide to 1 mole of the compound 5 in the presence of a catalytic amount of a metal fluoride (such as potassium fluoride or cesium fluoride) to obtain a compound 8b and thermally decomposing the compound 8b.

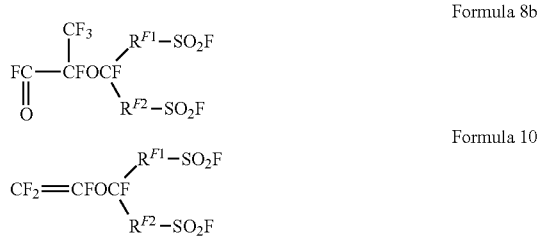

By the above-described methods for producing the compound 7, the compound 9 and the compound 10, monomers having two fluorosulfonyl groups in one molecule can be produced at a low cost, since the starting materials such as the compound 1 are inexpensive, and the yield on the compound 1 basis is high. The compound 7, the compound 9 and the compound 10 obtained by such methods are inexpensive as compared with conventional monomers having two fluorosulfonyl groups in one molecule. Further, the number of preparation steps of the compound 9-1 is smaller by two or one step than the method for producing a monomer described in Ex. 1 and 2 of Japanese Patent No. 5141251 (compound (m11) is produced by 8 steps from tetrafluoroethylene in Ex. 1, and compound (m12) is produced by 7 steps from tetrafluoroethylene in Ex. 2).

Further, the above-described compound 4 and compound 5 are useful as intermediates for the compound 7, the compound 9 and the compound 10. Various fluorosulfonyl group-containing monomers can be produced from the compound 4 and the compound 5.

Further, the compound 4 and the compound 5 can be produced at a low cost by the method for producing the compound 4 and the compound 5, since starting materials such as the compound 1 are inexpensive, and the yield on the compound 1 basis is high. Further, they can be produced by a smaller number of synthetic steps.

Fluorosulfonyl Group-Containing Polymer

A fluorosulfonyl group-containing polymer (hereinafter referred to also as "polymer F") is obtained by polymerizing the fluorosulfonyl group-containing monomer obtained by the production method of the present invention by a conventional polymerization method. For example, the polymer F has at least one member selected from the group consisting of units u1 based on the compound 7, units u2 based on the compound 9 and units u3 based on the compound 10. As the polymerization method, a bulk polymerization method, a solution polymerization method, a suspension polymerization method, an emulsion polymerization method, etc. may be mentioned. Further, the polymerization may be carried out in liquid or supercritical carbon dioxide.

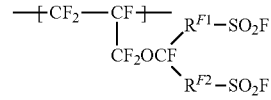

Formula u1

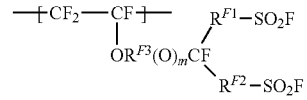

Formula u2

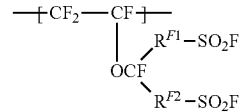

Formula u3

$R^{F1}$, $R^{F2}$, $R^{F3}$ and m are the same as $R^{F1}$, $R^{F2}$, $R^{F3}$ and m described in the compound 7 and the compound 9, and preferred forms are also the same.

For example, the polymer F may further have units based on tetrafluoroethylene (hereinafter referred to also as "TFE"). TFE has an effect to improve hydrophobicity of a polymer, whereby the after-described swelling is suppressed when the sulfonic acid group-containing polymer is hydrated, and the moisture content of the sulfonic acid group-containing polymer can be reduced. By reducing the moisture content, a polymer electrolyte membrane to be formed has a high mechanical strength. Further, when used in a catalyst layer, flooding of a polymer electrolyte fuel cell can be suppressed.

The polymer F may further have units based on a monomer other than the compound 7, the compound 9, the compound 10 and TFE.

Such other monomer may, for example, be chlorotrifluoroethylene, trifluoroethylene, vinylidene fluoride, vinyl fluoride, ethylene, propylene, perfluoro(3-butenyl vinyl ether), a perfluoro(allyl vinyl ether), a perfluoro α-olefin (such as hexafluoropropylene), a (perfluoroalkyl)ethylene (such as (perfluorobutyl)ethylene), a (perfluoroalkyl)propene (such as 3-perfluorooctyl-1-propene), a perfluoro(alkyl vinyl ether) or a perfluoromonomer having a 5-membered ring described in WO2011/013578.

In all units constituting the polymer F, the proportion of units u1, units u2 and units u3 based on the fluorosulfonyl group-containing monomer, units based on TFE and units based on other monomer may be appropriately determined depending on characteristics and physical properties required in applications of the sulfonic acid group-containing polymer, etc. (such as ion exchange capacity, ion conductivity, mechanical strength, elastic modulus, softening temperature, free volume, gas permeability, water vapor permeability, diffusibility of water, transport number, degree of swelling, size of phase separation structure, dispersible particle size in a liquid composition, viscosity of a liquid composition or storage elastic modulus of a liquid composition).

The volume flow rate (TQ value) of the polymer F is preferably from 200 to 330° C., more preferably from 205 to 260° C. When the TQ value of the polymer F is at least the lower limit value of the above range, the sulfonic acid group-containing polymer has a sufficient molecular weight and is excellent in the mechanical strength. When the TQ value of the polymer F is at most the upper limit value of the above range, the sulfonic acid group-containing polymer has good solubility or dispersability, and the after-mentioned liquid composition can be easily prepared. The TQ value is an index of the molecular weight of the polymer F.

The glass transition temperature (Tg) of the polymer F is preferably from 5 to 70° C., more preferably from 15 to 55° C. When Tg is at least the lower limit value of the above range, the tack property of the polymer F is suppressed, and the handling efficiency and the storage stability will be good. When Tg is at most the upper limit value of the above range, fragility of pellets or a membrane of the polymer F is suppressed.

The polymer F can be produced by polymerizing a monomer component containing at least one member selected from the group consisting of the compound 7, the compound 9 and the compound 10 and as the case requires, TFE and other monomer.

As the polymerization method, a bulk polymerization method, a solution polymerization method, a suspension polymerization method, an emulsion polymerization method, etc. may be mentioned. Further, the polymerization may be carried out in liquid or supercritical carbon dioxide.

The polymerization is carried out under conditions where radicals are formed. The method for forming radicals may, for example, be a method of applying radioactive rays such as ultraviolet rays, γ rays or electron rays or a method of adding a radical initiator. The polymerization temperature is preferably from 10 to 150° C.

The radical initiator may, for example, be bis(fluoroacyl) peroxide, bis(chlorofluoroacyl)peroxide, dialkyl peroxydicarbonate, diacyl peroxide, peroxyester, an azo compound or a persulfate. A perfluoro compound such as bis (fluoroacyl)peroxide is preferred, whereby a polymer F which has a few unstable terminal group is obtained.

The solvent used in the solution polymerization method is preferably a solvent having a boiling point of from 20 to 350° C., more preferably a solvent having a boiling point of from 40 to 150° C. The solvent may, for example, be a perfluorotrialkylamine (such as perfluorotributylamine), a perfluorocarbon (such as perfluorohexane or perfluorooctane), a hydrofluorocarbon (such as 1H, 4H-perfluorobutane or 1H-perfluorohexane), a hydrochlorofluorocarbon (such as 3,3-dichloro-1,1,1,2,2-pentafluoropropane or 1,3-dichloro-1,1,2,2,3-pentafluoropropane) or a hydrofluoroether (such as $CF_3CH_2OCF_2CF_2H$).

In the solution polymerization method, monomers, a radical initiator, etc. are added in a solvent, and radicals are formed in the solvent to polymerize the monomers. The monomers and the radical initiator may be added all at once, may be sequentially added or may be continuously added.

In the suspension polymerization method, it is preferred that water is used as a dispersion medium, monomers, a nonionic radical initiator, etc. are added in the dispersion medium to form radicals in the dispersion medium to polymerize the monomers.

The nonionic radical initiator may, for example, be a bis(fluoroacyl)peroxide, a bis(chlorofluoroacyl)peroxide, a dialkyl peroxydicarbonate, a diacyl peroxide, a peroxyester, a dialkyl peroxide, a bis(fluoroalkyl)peroxide or an azo compound.

An organic solvent as an assistant, a surfactant as a dispersion stabilizer to prevent aggregation of suspended particles or a hydrocarbon compound (such as hexane or methanol) as a molecular weight modifier may, for example, be added in the dispersion medium.

In the emulsion polymerization method, monomers are emulsified in water in the presence of an emulsifier and a polymerization initiator, and the monomers are polymerized. An the emulsifier and the polymerization initiator, those usually used for emulsion polymerization of a perfluoropolymer may be used. For example, as the emulsifier, an ammonium perfluorocarboxylate such as $CF_3CF_2CF_2CF_2OCF_2COONH_4$ or $CF_3CF_2OCF_2CF_2OCF_2COONH_4$ may be used. As the polymerization initiator, a radical initiator such as a peroxide, an azo compound or a persulfate may be used. Further, the initiator may be activated by an oxidation-reduction reaction with metal ions. Further, in addition, a buffer, a chain transfer agent, etc. used in a usual emulsion polymerization of a perfluoropolymer may be appropriately used. Further, a mixed liquid of an aqueous solvent and a fluorinated monomer may be forcibly emulsified by means of a homogenizer, a pressure emulsifier or the like before initiation of the polymerization in order to increase the reactivity of the fluorinated monomer.

The above-described polymer F has at least one member selected from the group consisting of units u1 based on the compound 7 having two fluorosulfonyl groups in one molecule, units u2 based on the compound 9 having two fluorosulfonyl groups in one molecule and units u3 based on the compound 10 having two fluorosulfonyl groups in one molecule, whereby a sulfonic acid group-containing polymer having a high ion exchange capacity can be obtained. Further, the polymer F has at least one member selected from the group consisting of units u1 based on the inexpensive compound 7, units u2 based on the inexpensive compound 9 and units u3 based on the inexpensive compound 10 and thereby is inexpensive as compared with conventional polymers having units based on a compound having two fluorosulfonyl groups in one molecule.

Sulfonic Acid Group-Containing Polymer

The obtained polymer F may be converted to a sulfonic acid group-containing polymer (hereinafter referred to also as "polymer H") by hydrolyzing sulfonyl groups into sulfonic acid groups by a known method. The acid form sulfonic acid groups in the polymer H may be converted to salt form sulfonic acid groups having a metal ion, an ammonium ion or the like depending on applications. The polymer H is a polymer obtained by converting fluorosulfonyl groups in the polymer F into sulfonic acid groups and for example, has at least one member selected from the group consisting of units u4 derived from units u1, units u5 derived from units u2 and units u6 derived from units u3.

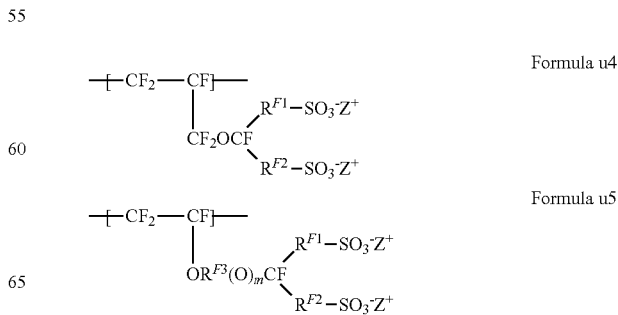

-continued

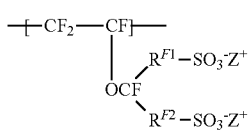

Formula u6 wherein $Z^4$ is $H^+$, a metal ion or an ammonium ion. The metal ion is preferably an alkali metal.

$R^{F1}$, $R^{F2}$, $R^{F3}$ and m are the same as $R^{F1}$, $R^{F2}$, $R^{F3}$ and m described in the compound 7 and the compound 9, and preferred forms are also the same.

The polymer H preferably further has units based on TFE. The polymer H may further have units based on a monomer other than the compound 7, the compound 9, the compound 10 and TFE.

The polymer H preferably has an ion exchange capacity of from 0.5 to 2.5 meq/g dry resin (hereinafter the unit "meq/g dry resin" may be omitted in some cases), more preferably from 1.3 to 2.3. When the ion exchange capacity is at least the lower limit value of the above range, the polymer H has a high ion conductivity, whereby when used in a polymer electrolyte membrane or a catalyst layer for a polymer electrolyte fuel cell, sufficient power output can be obtained. Further, when used in an ion exchange membrane for alkali chloride electrolysis or water electrolysis, overvoltage of a membrane resistance or the like is lowered, whereby an electric power consumption rate can be reduced. When the ion exchange capacity is at most the upper limit value of the above range, swelling is suppressed when the polymer H absorbs water, whereby a polymer electrolyte membrane to be formed has a high mechanical strength. Further, when used as a catalyst layer, flooding of a polymer electrolyte fuel cell is suppressed.

The polymer H has a softening temperature of preferably from 100 to 180° C., more preferably from 120 to 170° C., further preferably from 140 to 160° C. When the softening temperature is at least the lower limit value of the above range, a polymer electrolyte membrane to be formed has a high mechanical strength at a high temperature. When the softening temperature is at most the upper limit value of the above range, the temperature for annealing treatment of a polymer electrolyte membrane or thermal press required for transferring a catalyst layer or forming a membrane/electrode assembly is made to be low.

The polymer H has a moisture content (mass basis) of preferably from 30 to 300%, more preferably from 40 to 200%. When the moisture content is at least the lower limit value of the above range, the polymer H has a high ion conductivity, whereby a membrane/electrode assembly which is further excellent in power generation performance can be obtained. When the moisture content is at most the upper limit value of the above range, the polymer H will not extensively swell by water, whereby the mechanical strength of a polymer electrolyte membrane can be maintained.

The polymer H is obtained by converting fluorosulfonyl groups in the polymer F into sulfonic acid groups. As a method of converting fluorosulfonyl groups into sulfonic acid groups, a method may be mentioned that fluorosulfonyl groups in the polymer F are hydrolyzed into salt form sulfonic acid groups, and the salt form sulfonic acid groups are converted into acid form so as to be acid form sulfonic acid groups. In a case where the salt form sulfonic acid groups are desired, conversion into acid form is not carried out.

The hydrolysis is carried out, for example, by bringing the polymer F into contact with a basic compound in a solvent. The basic compound may, for example, be sodium hydroxide, potassium hydroxide or triethylamine. The solvent may, for example, be water or a mixed solvent of water and a polar solvent. The polar solvent may, for example, be an alcohol (such as methanol or ethanol) or dimethylsulfoxide.

Conversion into acid form may, for example, be carried out by bringing the polymer H having salt form sulfonic acid groups into contact with an aqueous solution of e.g. hydrochloric acid or sulfuric acid. The temperature in the hydrolysis and conversion into acid form is preferably from 0 to 120° C. After the hydrolysis or conversion into acid form, the polymer H is preferably washed with water.

In order to remove organic substances contained as impurities in the polymer H, the polymer H may be subjected to treatment of e.g. immersing in a hydrogen peroxide solution to decompose the organic substances after the hydrolysis or conversion into acid form. Sulfonic acid groups in the polymer H may be salt form or acid form. The polymer H may be in a powder form, a pellet form or a membrane form.

The concentration of hydrogen peroxide in the hydrogen peroxide solution is preferably from 0.1 to 30 mass %, more preferably at least 1 mass % and less than 10 mass %. When the concentration of hydrogen peroxide is at least the lower limit value of the above range, the effect to decompose organic substances is sufficient. When the concentration of hydrogen peroxide is at most the upper limit value of the above range, the polymer H is less likely to be decomposed.

The temperature of the hydrogen peroxide solution is preferably from 15 to 90° C., more preferably at least 40° C. and less than 80° C. When the temperature of the hydrogen peroxide solution is at least the lower limit value of the above range, the effect to decompose organic substances is sufficient. When the temperature of the hydrogen peroxide solution is at most the upper limit value of the above range, hydrogen peroxide is less likely to be decomposed.

Time for immersing the polymer H in the hydrogen peroxide solution is, for example, preferably from 0.5 to 100 hours in a case where the polymer H has a thickness of 50 μm, although it depends on the thickness of the polymer H and the amount of organic substances contained. If the time for immersing is less than 0.5 hour, organic substances in the inside of a membrane are hardly decomposed. If the polymer H is immersed over 100 hours, the effect to further decompose organic substances is not expected.

The polymer H is preferably washed with water after immersed in the hydrogen peroxide solution. Water to be used for washing is preferably ultrapure water. Further, before washing with water, treatment for conversion into acid form may be carried out.

As applications of the polymer H, a polymer contained in a liquid composition for forming a membrane containing a polymer, a polymer contained in a catalyst layer or a polymer electrolyte membrane for a membrane/electrode assembly for a polymer electrolyte fuel cell, a polymer contained in a catalyst layer or a polymer electrolyte membrane in a membrane/electrode assembly for a polymer electrolyte water electrolysis, a polymer contained in a cation exchange membrane to be used for alkali chloride electrolysis or electrodialysis, a polymer contained in a diaphragm for a redox flow secondary cell, a polymer contained in an ion exchange membrane to be used for alkali water electrolysis or PEM type water electrolysis, a polymer contained in an ion exchange membrane for an electrochemical hydrogen pump, a polymer contained in a cation exchange resin to be used in an ion conductive polymer actuator or a gas sensor, a polymer to be used for a solid acid catalyst, a polymer to be used for a film type humidity controlling apparatus such as a dehumidifier or a humidifier, a polymer to be used in a gas barrier membrane, etc. may be mentioned.

The above-described polymer H can be produced at a low cost since the fluorosulfonyl group-containing monomer as a starting material can be produced at a low cost, and has a large number of acid form or salt form sulfonic acid groups and thereby has a high ion exchange capacity, whereby when used as a membrane, the membrane has a high ion exchange capacity and excellent ion conductivity.

Liquid Composition

The liquid composition of the present invention comprises the polymer H and a liquid medium.

The liquid composition of the present invention may be one having the polymer H dispersed in a liquid medium or one having the polymer H dissolved in a liquid medium.

The liquid medium may be water alone, an organic solvent alone or one containing water and an organic solvent, and is preferably one containing water and an organic solvent.

Water improves the dispersability or solubility of the polymer H in the liquid medium.

A catalyst layer and a polymer electrolyte membrane which are not fragile can be easily formed with the organic solvent.

The organic solvent is preferably at least one $C_{1-4}$ alcohol with a view to easily forming a catalyst layer and a polymer electrolyte member which are not fragile.

The $C_{1-4}$ alcohol may, for example, be methanol, ethanol, 1-propanol, 2-propanol, 1-butanol, 2,2,2-trifluoroethanol, 2,2,3,3,3-pentafluoro-1-propanol, 2,2,3,3-tetrafluoro-1-propanol, 1,1,1,3,3,3-hexafluoro-2-propanol or 3,3,3-trifluoro-1-propanol.

The proportion of water in the liquid composition is preferably from 10 to 99 mass %, more preferably from 20 to 99 mass % to the sum of water and the organic solvent. The proportion of the organic solvent is preferably from 1 to 90 mass %, more preferably from 1 to 80 mass % to the sum of water and the organic solvent.

When the proportions of water and the organic solvent fall within the above ranges, the polymer H has excellent dispersability in a dispersion medium, and a catalyst layer and a polymer electrolyte membrane which are not fragile can be easily formed.

The concentration of the polymer H in the liquid composition is preferably from 1 to 50 mass %, more preferably from 3 to 30 mass %. When the concentration is at least the lower limit value of the above range, a thick membrane can be stably obtained when forming a membrane. Further, the composition of a coating liquid for forming a catalyst layer can be easily adjusted when producing a catalyst layer. When the concentration is at most the upper limit value of the above range, it can be suppressed that the liquid composition has an excessively high viscosity.

The liquid composition may have at least one metal, metal compound or metal ion selected from the group consisting of cerium and manganese in order to further improve the durability of a polymer electrolyte membrane and a catalyst layer to be produced from the liquid composition.

The liquid composition is obtained by mixing the polymer H and the liquid medium.

The mixing method may, for example, be a method of applying shearing force such as stirring to the polymer H in the liquid medium under atmospheric pressure or under a sealed state by an autoclave or the like.

The temperature at the time of stirring is preferably from 0 to 250° C., more preferably from 20 to 150° C. As the case requires, shearing force such as ultrasonic wave may be applied.

When applying shearing force such as stirring to a mixed liquid of the polymer H and the liquid medium, shearing force such as stirring may be applied to a mixed liquid in which the liquid medium is added all at once to the polymer H, or the liquid medium is dividedly mixed with the polymer H plural times, and shearing force such as stirring may be applied during intervals. For example, shearing force such as stirring is applied to a mixed liquid in which a part of the liquid medium is added to the polymer H and the rest of the liquid medium is added to the mixed liquid, and shearing force such as stirring is applied again. Otherwise, only an organic solvent is added to the liquid medium and shearing force such as stirring is applied, and then only water is added, and shearing force such as stirring is applied again.

The above-described liquid composition has a high ion exchange capacity and contains the polymer H which is inexpensive as compared with conventional one, whereby a membrane containing a polymer having a high ion exchange capacity can be formed, which is in expensive as compared with conventional one.

Membrane

The membrane of the present invention contains the polymer H and may further contain a reinforcing material. The membrane of the present invention may further contain components other than the polymer H and the reinforcing material.

The reinforcing material may, for example, be a porous body, fibers, a woven fabric or a non-woven fabric. As the material of the reinforcing material, various polymers may be mentioned and may be appropriately selected depending on applications of the membrane. In a case where the membrane is a polymer electrolyte membrane in a membrane/electrode assembly for a polymer electrolyte fuel cell, the material of the reinforcing material may, for example, be a polytetrafluoroethylene, a tetrafluoroethylene/hexafluoropropylene copolymer, a tetrafluoroethylene/perfluoro(alkyl vinyl ether) copolymer, a polyethylene, a polypropylene or a polyphenylene sulfide.

The method for producing the membrane of the present invention may, for example, be a method (cast method) of applying the liquid composition of the present invention on a substrate, followed by drying, or a method of extruding the polymer F into a membrane form and converting fluorosulfonyl groups into sulfonic acid groups. In a case where the reinforcing material is further contained, a method of immersing the liquid composition of the present invention in the reinforcing material, followed by drying may be mentioned.

In a case where the membrane is a polymer electrolyte membrane in a membrane/electrode assembly for a polymer electrolyte fuel cell, the polymer electrolyte membrane may, for example, be formed by a method of applying the liquid composition on a substrate film or a catalyst layer, followed by drying.

In a case where the membrane is a catalyst layer in a membrane/electrode assembly for a polymer electrolyte fuel cell, the catalyst layer may be formed by a method of applying a catalyst layer-forming coating liquid on a polymer electrolyte membrane, a gas diffusion layer or the like, followed by drying or a method of applying a catalyst layer-forming coating liquid on a substrate film, followed by drying to form a catalyst layer and transferring the catalyst layer on a polymer electrolyte membrane. The catalyst layer-forming coating liquid may, for example, be prepared by mixing the liquid composition of the present invention and a dispersion of a catalyst.

The application of the membrane of the present invention may, for example, be a catalyst layer or a polymer electrolyte membrane in a membrane/electrode assembly for a polymer electrolyte fuel cell, a catalyst layer or a polymer electrolyte membrane in a membrane/electrode assembly for a polymer electrolyte water electrolysis, a cation exchange membrane to be used for alkali chloride electrolysis or electrodialysis, an ion exchange membrane to be used for water electrolysis, a diaphragm for a redox flow secondary cell or an ion exchange membrane for an electrochemical hydrogen pump.

As described above, the membrane of the present invention has a high ion exchange capacity and contains the polymer H which is inexpensive as compared with conventional one and thereby contains a polymer having a high ion exchange capacity and is inexpensive as compared with conventional one.

EXAMPLES

Now, the present invention will be described with reference to Examples, but the present invention is not limited thereto. Further, Ex. 1 is an Example of the present invention, and Ex. 2 to 13 are Reference Examples.

$^1$H-NMR $^1$H-NMR was measured under conditions of frequency of 300.4 MHz and chemical shift reference of tetramethylsilane. Unless otherwise specified, $CD_3CN$ was used as a solvent. The quantitative measurement of a product was conducted by results of $^1$H-NMR analysis and the amount of an added internal standard sample (1,3-bis(trifluoromethyl)benzene).

$^{19}$F-NMR $^{19}$F-NMR was measured under conditions of frequency of 282.7 MHz, a solvent of $CD_3CN$ and chemical shift reference of $CFCl_3$. The quantitative measurement of a product was conducted by results of $^{19}$F-NMR and the amount of an added internal standard sample (1,3-bis(trifluoromethyl)benzene).

$^{13}$C-NMR $^{13}$C-NMR was measured under conditions of frequency of 75.5 MHz and chemical shift reference of tetramethylsilane. Unless otherwise specific, $CD_3CN$ was used as a solvent.

Yield

The yield is (yield of a reaction step)×(yield of a purification step), and the reaction yield is the yield of a reaction step before purifying a desired product, which excludes the loss in the purification step.

Ion Exchange Capacity

A membrane of a polymer (polymer F or polymer H) was vacuum dried at 120° C. for 12 hours. The mass of the dried membrane of the polymer was measured, and then the membrane of the polymer was immersed in a 0.85 mol/g sodium hydroxide solution (solvent: water/methanol=10/90 (mass ratio)) to hydrolyze ion exchange groups. The sodium hydroxide solution after the hydrolysis was back titrated with 0.1 mol/L hydrochloric acid to obtain the ion exchange capacity (meq/g dry resin) of the polymer.

Proportion of Units Based on Fluorosulfonyl Group-Containing Monomer

The proportions of units based on the fluorosulfonyl group-containing monomer ($SO_2F$ group-containing monomer) in the polymer F was calculated from the ion exchange capacity of the polymer F.

TQ Value

The polymer F was melt extruded by means of a flow tester (CFT-500A, manufactured by Shimadzu Corporation) provided with a nozzle having a length of 1 mm and an internal diameter of 1 mm under an extrusion pressure of 2.94 MPa (gage pressure) while changing the temperature. The temperature (TQ value) at which the extruded amount of the polymer F became 100 mm$^3$/s was obtained. The higher the TQ value is, the larger the molecular weight of the polymer is.

Measurement of Dynamic Viscoelasticity

The dynamic viscoelasticity of the membrane of the polymer F or the membrane of the polymer H was measured by means of a dynamic viscosity measuring apparatus (DVA-225, manufactured by IT Keisoku Seigyo) under conditions of test specimen width: 5.0 mm, length of specimen between grips: 15 mm, measuring frequency: 1 Hz, rate of temperature rise: 2° C./min and a tensile mode. Tan σ (loss tangent) was calculated from the ratio (E"/E') of the loss elastic modulus E" to the storage elastic modulus E', and tan σ-temperature curve was drawn. The value of a peak temperature between −100 to 200° C. on the tan σ-temperature curve is Tg of the polymer F or a softening temperature of the polymer H. Further, a storage elastic modulus E'-temperature curve was drawn, and a value of the storage elastic modulus at 120° C. was taken as a 120° C. storage elastic modulus of the polymer H.

Conductivity

To a membrane of the polymer H having a thickness of 25 μm and a width of 5 mm, a substrate provided with 4 terminal electrodes at an interval of 5 mm was contact-bonded by known four probe method, and the resistance of the membrane of the polymer H was measured at an alternative current: 10 kHz and a voltage: 1 V under the constant temperature and constant humidity conditions of temperature: 80° C. and relative humidity of 50% to calculate the conductivity.

Moisture Content

The membrane of the polymer H was immersed in warm water of 80° C. for 16 hours and cooled until the water temperature reached at most 25° C. The membrane of the polymer H was taken out, water droplets attached on a surface of the membrane were wiped away by a filter paper, and the mass W1 of the membrane of the polymer H was measured. The membrane of the polymer H was dried in a glove box under a nitrogen atmosphere for 48 hours, and then the mass W2 of the membrane of the polymer H was measured in the glove box. The moisture content (mass standard) was obtained by the following formula I.

Moisture content=$(W1-W2)/W2\times 100$   Formula 1

Abbreviations

PSVE: $CF_2$=$CFOCF_2CF(CF_3)OCF_2CF_2SO_2F$,
P2SVE: $CF_2$=$CFOCF_2CF(CF_2OCF_2CF_2SO_2F)OCF_2CF_2SO_2F$,
PDD: perfluoro-2,2-dimethyl-1,3-dioxole,
PMVE: perfluoro(methyl vinyl ether),
PFtBPO: $(CF_3)_3COOC(CF_3)_3$,
AIBN: $(CH_3)_2C(CN)N$=$NC(CH_3)_2(CN)$,
IPP: $(CH_3)_2CHOC(O)OOC(O)OCH(CH_3)_2$,
V-601: $CH_3OC(O)C(CH_3)_2$—N=N—$C(CH_3)_2C(O)OCH_3$,
PFB: $(C_3F_7C(O)O)_2$,
HFC-52-13p: $CF_3(CF_2)_5H$,
HFE-347pc-f: $CF_3CH_2OCF_2CF_2H$,
HCFC-225cb: $CClF_2CF_2CHClF$,
HCFC-141b: $CH_3CCl_2F$.

Ex. 1

Ex. 1-1

560 g of chlorosulfuric acid was charged in a 2 L four-necked flask provided with a stirrer, a condenser, a thermometer and a dropping funnel under nitrogen gas sealing. The flask was cooled in an ice bath, and a mixed liquid of 139.5 g of the compound 1-1 and 478.7 g of dichloromethane was dropwise added over 20 minutes, while maintaining the internal temperature at 20° C. Heat generation and generation of gas were observed at the time of the dropwise addition. After completion of the dropwise addition, the flask was set in an oil bath, and a reaction was carried out for 7 hours while maintaining the internal temperature at from 30 to 40° C. The reaction proceeded with the generation of gas, and a white solid precipitated. After the reaction, the inside of the flask was decompressed to distill dichloromethane off. A yellowish white solid remained in the flask. The solid was analyzed by $^1$H-NMR, and formation of compound 2-1 was confirmed.

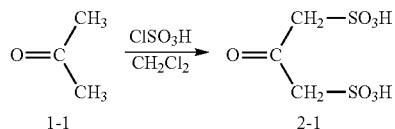

NMR spectrum of compound 2-1;
$^1$H-NMR (solvent: D20): 4.27 ppm (—$CH_2$—, 4H, s)
$^{13}$C-NMR (solvent: D20): 62.6 ppm (—$CH_2$—), 195.3 ppm (C=O)

Ex. 1-2

The compound 2-1 obtained in Ex. 1-1 was used in a subsequent reaction as it was without being isolated. 2,049 g of thionyl chloride was added in the flask of Ex. 1-1. The flask was heated to 80° C., followed by reflux for 15 hours. Along with the progress of the reaction, the reflux temperature increased from 52° C. to 72° C. The generation of gas was observed during the reaction. The termination of the reaction was when the compound 2-1 was entirely dissolved, and the generation of gas terminated. The reaction liquid was transferred to a 2 L separable flask, and the flask was left to cool for 9 hours while a gas phase part was sealed with nitrogen gas, and as a result, a blackish brown solid precipitated in the separable flask. Unreacted thionyl chloride was removed by decantation. Toluene was added to wash the precipitated solid, and toluene was removed by decantation again. Washing with toluene was carried out three times in total, and the amount of used toluene was 1,207 g in total. The precipitated solid was dried at 25° C. for 71 hours under nitrogen gas stream. The dried solid was recovered and analyzed by $^1$H-NMR, and it was confirmed that 356.5 g of compound 3-1 with a purity of 96.2% was obtained. The yield on the compound 1-1 basis was 56.0%.

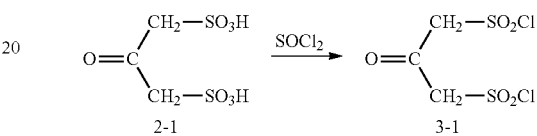

NMR spectrum of compound 3-1;
$^1$H-NMR: 5.20 ppm (—$CH_2$—, 4H, s)
$^{13}$C-NMR: 72.3 ppm (—$CH_2$—), 184.6 ppm (C=O)

Ex. 1-3

90.0 g of the compound 3-1 and 750 mL of acetonitrile were charged in a 1 L four-necked flask provided with a stirrer, a condenser and a thermometer under nitrogen gas sealing. The flask was cooled in an ice bath, and 110.3 g of potassium hydrogen fluoride was added with stirring. Heat generation due to the addition was slight. The ice bath was changed to a water bath, and a reaction was carried out for 62 hours while maintaining the internal temperature at from 15 to 25° C. Along with the reaction, fine white solids formed. The reaction liquid was transferred to a pressure filter, and unreacted potassium hydrogen fluoride was removed from the product by filtration. Acetonitrile was added to the filter, the solid remaining on the filter was washed until the filtrate became transparent, and the wash was recovered. The filtrate and the wash were subjected to an evaporator to distill acetonitrile off. 950 mL of toluene was added to the remaining dried solid, followed by heating to 100° C. to dissolve the solid in toluene. The solution was natural filtered to remove undissolved components. The filtrate was transferred to a 1 L separable flask, and the flask was left to cool for 14 hours while a gas phase part was sealed with nitrogen gas, and as a result, pale brown needle crystals precipitated in the separable flask. The crystals were washed with toluene and dried at 25° C. for 30 hours under nitrogen gas stream. The dried solid was recovered and analyzed by $^1$H-NMR and $^{19}$F-NMR, and as a result, it was confirmed that 58.1 g of compound 4-1 with a purity of 97.6% was obtained. The yield on the compound 3-1 basis was 72.3%.

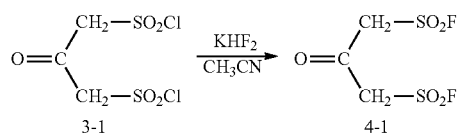

NMR spectrum of compound 4-1;
$^1$H-NMR: 4.97 ppm (—CH$_2$—, 4H, d, J=3.1 Hz)
$^{19}$F-NMR: 62.4 ppm (—SO$_2$F, 2F, t, J=3.1 Hz)
$^{13}$C-NMR: 60.7 ppm (—CH$_2$—), 184.9 ppm (C=O)

Ex. 1-4

9.93 g of the compound 4-1 and 89.7 g of acetonitrile were charged in a 200 mL autoclave made of nickel. The autoclave was cooled, nitrogen gas was fed at a flow rate of 6.7 L/hr while maintaining the internal temperature at from 0 to 5° C., and the reaction liquid was bubbled for 1 hours. While maintaining the temperature of the reaction liquid at from 0 to 5° C., a mixed gas of fluorine gas and nitrogen gas (mixing ratio=10.3 mol %/89.7 mol %) was introduced over 6 hours at a flow rate of 6.7 L/hr. Nitrogen gas was fed again at a flow rate of 6.7 L/hr, and the reaction liquid was bubbled for 1 hour. 103.2 g of the reaction liquid was recovered from the autoclave. The reaction liquid was analyzed by $^{19}$F-NMR, and it was confirmed that 8.4 mass % of compound 5-1 and 3.2 mass % of hydrogen fluoride were contained. The reaction yield on the compound 4-1 basis was 66%.

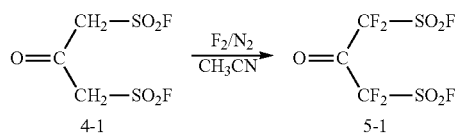

NMR spectrum of compound 5-1 (in the presence of hydrogen fluoride):
$^{19}$F-NMR: −104.1 ppm (—CF$_2$—, 4F, s), 45.8 ppm (—SO$_2$F, 2F, s)

Ex. 1-5

19.9 g of the compound 4-1 and 85.6 g of acetonitrile were charged in a 200 mL autoclave made of nickel. The autoclave was cooled, nitrogen was fed at a flow rate of 6.7 L/hr while maintaining the internal temperature at from 0 to 5° C., and the reaction liquid was bubbled for 1 hour. While maintaining the temperature of the reaction liquid at from 0 to 5° C., a mixed gas of fluorine gas and nitrogen gas (mixing ratio=10.3 mol %/89.7 mol %) was introduced at a flow rate of 16.4 L/hr over 6.5 hours. Nitrogen gas was fed again at a flow rate of 6.7 L/hr, and the reaction liquid was bubbled for 1 hour. 109.6 g of the reaction liquid containing the compound 5-1 was recovered from the autoclave.

Ex. 1-6

20.1 g of the compound 4-1 and 80.1 g of acetonitrile were charged in a 200 mL autoclave made of nickel. The autoclave was cooled, nitrogen gas was fed at a flow rate of 6.7 L/hr while maintaining the internal temperature at from 0 to 5° C., and the reaction liquid was bubbled for 1 hour. While maintaining the temperature of the reaction liquid at from 0 to 5° C., a mixed gas of fluorine gas and nitrogen gas (mixing ratio=20.0 mol %/80.0 mol %) was introduced at a flow rate of 8.4 L/hr over 6 hours. Nitrogen gas was fed again at a flow rate of 6.7 L/hr, and the reaction liquid was bubbled for 1 hour. 107.1 g of the reaction liquid containing the compound 5-1 was recovered from the autoclave.

Ex. 1-7

1.65 g of potassium fluoride and 7.8 mL of diethylene glycol dimethyl ether (diglyme) were charged in a 50 mL four-necked flask provided with a stirrer, a condenser, a thermometer and a dropping funnel. The flask was cooled in an ice bath, and 8.43 g of the reaction liquid obtained in Ex. 1-4 was dropwise added by means of a plastic syringe while maintaining the internal temperature at from 0 to 10° C. by stirring. Intense heat generation was observed, and 15 minutes was spent for the dropwise addition. After completion of the dropwise addition, the ice bath was changed to a water bath, and the reaction was carried out for 1 hour at from 15 to 20° C. The flask was cooled in an ice bath again, and 6.56 g of compound 6-1 was dropwise added from a dropping funnel while maintaining the temperature of the reaction liquid at from 0 to 10° C. After completion of the dropwise addition, the ice bath was changed to a water bath, and the reaction was carried out for 3.5 hours at from 20 to 25° C. By-products were removed from the reaction liquid by suction filtration to recover the filtrate. The solid removed by filtration was washed with an appropriate amount of acetonitrile, and the wash and the filtrate were mixed. 37.1 g of the filtrate was quantitatively analyzed by $^{19}$F-NMR, and it was confirmed that 2.04 mass % of compound 7-1 was contained. The reaction yield on the compound 4-1 basis was 46.6%.

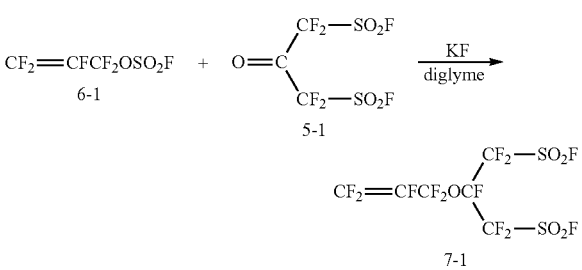

NMR spectrum of compound 7-1;
$^{19}$F-NMR: −191.5 ppm (CF$_2$=CF—, 1F, ddt, J=116, 38, 14 Hz), −133.8 ppm (—O—CF—, 1F. t, J=21.3, 6.1 Hz), −103.1 ppm (—CF$_2$—SO$_2$F, 4F, m), −101.5 ppm (CF$_2$=CF—, 1F, ddt, J=116, 49, 27 Hz), −87.6 ppm (CF$_2$=CF—, 1F, ddt, J=49, 38, 7 Hz), −67.5 ppm (—CF$_2$—O—, 2F, m), 46.8 ppm (—SO$_2$F, 2F, s).

Ex. 1-8

36.6 g of potassium fluoride and 125.6 g of acetonitrile were charged in a 500 mL four-necked flask provided with a stirrer, a condenser, a thermometer and a dropping funnel. The flask was cooled in an ice bath, and 79.8 g of the reaction liquid obtained in Ex. 1-5 was dropwise added by means of a dropping funnel made of a plastic while maintaining the internal temperature at from 0 to 10° C. by stirring. Intense heat generation was observed, and 23 minutes was spent for the dropwise addition. After completion of the dropwise addition, the ice bath was changed to a water bath, and the reaction was carried out for 5.5 hour at from 20 to 30° C. The flask was cooled in an ice bath again, and 146.0 g of the compound 6-1 was dropwise added from a dropping funnel while maintaining the temperature of the reaction liquid at from 0 to 10° C. After completion of the dropwise addition, the ice bath was changed to a water bath, and the reaction was carried out for 16 hours at from 15 to 25° C. Suction filtration was carried out in the same manner as in Ex. 7-1, and 412.3 g of the obtained filtrate was quantitatively analyzed by $^{19}$F-NMR, and it was confirmed that 3.93 mass % of the compound 7-1 was contained. The reaction yield on the compound 4-1 basis was 55.9%. The filtrate was distilled off under reduced pressure to isolate the compound 7-1 as a fraction with a boiling point of 97.2° C./10 KPa. The purity by gas chromatography was 98.0%.

Ex. 1-9

3.70 g of potassium fluoride and 10.9 g of acetonitrile were charged in a 50 mL four-necked flask provided with a stirrer, a condenser, a thermometer and a dropping funnel. The flask was cooled in an ice bath, and 10.2 g of the reaction liquid obtained in Ex. 1-6 was dropwise added by means of a plastic syringe while maintaining the internal temperature at from 0 to 10° C. by stirring. Intense heat generation was observed, and 8 minutes was spent for the dropwise addition. After completion of the dropwise addition, the ice bath was changed to a water bath, and the reaction was carried out for 3 hours at from 20 to 30° C. The flask was cooled in an ice bath again, and 14.6 g of the compound 6-1 was dropwise added from a dropping funnel while maintaining the temperature of the reaction liquid at from 0 to 10° C. After completion of the dropwise addition, the ice bath was changed to a water bath, and the reaction was carried out for 17 hours at from 15 to 25° C. Suction filtration was carried out in the same manner as in Ex. 7-1, and 55.9 g of the obtained filtrate was quantitatively analyzed by $^{19}$F-NMR, and it was confirmed that 4.77 mass % of the compound 7-1 was contained. The reaction yield on the compound 4-1 basis was 69.6%. Further, the reaction yield on the compound 1-1 basis (the reaction yield in all steps for preparing the monomer) was 28.2%.

Ex. 2

Ex. 2-1

70.0 g of the compound 7-1 was added in an autoclave (internal capacity of 100 mL and made of stainless steel), followed by cooling and deaerating by liquid nitrogen. 2.53 g of TFE was introduced in the autoclave, and the autoclave was heated in an oil bath until the internal temperature reached 100° C. The pressure at that time was 0.29 MPaG (gage pressure). A mixed liquid of 36.3 mg of PFtBPO as a polymerization initiator and 2.58 g of HFC-52-13p was injected into the autoclave. Further, nitrogen gas was introduced from an injection line to completely inject the liquid in the injection line into the autoclave. TFE in the gas phase part was diluted by this operation, and as a result, the pressure increased to 0.56 MPaG. While maintaining the pressure at 0.56 MPaG, TFE was continuously added to carry out polymerization. The inside of the autoclave was cooled to terminate the polymerization, when the added amount of TFE reached 4.03 g after 9.5 hours, and the gas in the system was purged. The reaction liquid was diluted with HFC-52-13p, HFE-347pc-f was added to aggregate the polymer, and the polymer was filtered. Then, an operation of stirring the polymer in HFC-52-13p and aggregating the polymer with HFE-347pc-f again was repeated twice. Vacuum drying at 120° C. was carried out to obtain polymer F-1 which is a copolymer of TFE and the compound 7-1. Results are shown in Table 1.
(Ex. 2-2 to Ex. 2-5)
Polymer F-2 to polymer F-5 were obtained in the same manner as in Ex. 2-1, except that conditions were changed as shown in Table 1 (in Ex. 2-2, 34.0 g of HFC-52-13p was charged with the compound 7-1, and 2.9 g was used to prepare a mixed liquid with the polymerization initiator, and in Ex. 2-3 to Ex. 2-5, without initially charging TFE, and instead, after heating to the polymerization temperature, TFE was injected until the pressure reached the pressure prior to nitrogen gas dilution as shown in Table 1). Results are shown in Table 1.

TABLE 1

| | Ex. 2-1 | Ex. 2-2 | Ex. 2-3 | Ex. 2-4 | Ex. 2-5 |
| --- | --- | --- | --- | --- | --- |
| Obtained polymer F | F-1 | F-2 | F-3 | F-4 | F-5 |
| Capacity of reactor [mL] | 100 | 100 | 100 | 100 | 100 |
| Compound 7-1 [g] | 70.0 | 31.5 | 103.0 | 80.0 | 82.0 |
| Initially charged TFE [g] | 2.53 | 2.44 | — | — | — |
| HFC-52-13p [g] | 2.58 | 36.9 | 6.46 | 4.23 | 4.18 |
| Polymerization initiator | PFtBPO | PFtBPO | PFtBPO | PFtBPO | PFtBPO |
| Amount of polymerization initiator [mg] | 36.3 | 34.3 | 105.8 | 41.4 | 42.3 |
| Polymerization temperature [° C.] | 100 | 100 | 100 | 100 | 100 |
| Pressure prior to nitrogen gas dilution [MPaG] | 0.29 | 0.27 | 0.10 | 0.29 | 0.25 |
| Polymerization pressure [MPaG] | 0.56 | 0.56 | 0.60 | 0.56 | 0.49 |
| Continuously added TFE [g] | 4.03 | 4.29 | 3.84 | 5.59 | 6.49 |
| Polymerization time [hr] | 9.5 | 8.5 | 12.5 | 6.9 | 10.0 |
| Yield of polymer F [g] | 6.4 | 4.6 | 7.61 | 8.47 | 10.0 |
| Ion exchange capacity [meq/g dry resin] | 1.87 | 1.49 | 2.37 | 1.78 | 1.90 |
| Units based on compound 7-1 [mol %] | 13.8 | 10.0 | 19.9 | 12.4 | 14.0 |
| Units based on compound 7-1 [mass %] | 41.2 | 32.8 | 52.2 | 38.4 | 41.8 |
| TQ value [° C.] | 238 | 268 | 158 | 298 | 314 |
| Tg [° C.] | 39 | 43 | 33 | 41 | 39 |

Ex. 3

Ex. 3-1 to Ex. 3-5

Membranes of polymers H-1 to H-5 were obtained by the following method using the polymers F-1 to F-5.

A polymer F was press molded at a temperature higher by 10° C. than TQ value (260° C. in Ex. 3-4 and Ex. 3-5) under 4 MPa (gage pressure) to obtain a membrane (thickness of from 100 to 250 μm) of the polymer F. The membrane of the polymer F was immersed in an alkali aqueous solution as shown in Table 2 at 80° C. for 16 hours to hydrolyze and thereby convert —SO$_2$F groups in the polymer F into —SO$_3$K groups. Further, the membrane of the polymer was immersed in a 3 mol/L hydrochloric acid aqueous solution at 50° C. for 30 minutes and then immersed in ultrapure water at 80° C. for 30 minutes. A cycle of immersing in a hydrochloric acid aqueous solution and immersing in ultrapure water was carried out five times in total to convert —SO$_3$K groups in the polymer into —SO$_3$H groups. The washing with ultrapure water was repeated, until pH of water in which the membrane of the polymer was immersed became 7. The membrane of the polymer was sandwiched between filter papers and air-dried to obtain a membrane of polymer H. Results are shown in Table 2.

TABLE 2

|  | Ex. 3-1 | Ex. 3-2 | Ex. 3-3 | Ex. 3-4 | Ex. 3-5 |
|---|---|---|---|---|---|
| Used polymer F | F-1 | F-2 | F-3 | F-4 | F-5 |
| Obtained polymer H | H-1 | H-2 | H-3 | H-4 | H-5 |
| Used alkali aqueous solution | Aqueous solution A | Aqueous solution B | Aqueous solution A | Aqueous solution C | Aqueous solution A |
| Softening temperature [° C.] | 147 | 151 | 151 | 151 | 153 |
| Elastic modulus at 120° C. [MPa] | 95.7 | 160 | 72.1 | 119 | 117 |
| Conductivity [S/cm] | 0.136 | 0.080 | 0.164 | 0.123 | 0.136 |
| Moisture content [%] | 136 | 48 | At least 400 | 93 | 110 |

In Table 2, "aqueous solution A" is potassium hydroxide/water=20/80 (mass ratio), "aqueous solution B" is potassium hydroxide/dimethylsulfoxide/water=15/30/55 (mass ratio), and "aqueous solution C" is potassium hydroxide/methanol/water=15/20/65 (mass ratio). Further, these definitions are also applied to the after-described Table 4.

Ex. 4

Ex. 4-1

123.8 g of PSVE, 35.2 g of HCFC-225cb and 63.6 mg of AIBN were added in a hastelloy autoclave having an internal capacity of 230 mL, followed by cooling and deaeration by liquid nitrogen. The temperature was raised to 70° C., and TFE was introduced in the system to maintain the pressure at 1.14 MPaG. TFE was continuously added so as to maintain the constant pressure at 1.14 MPaG. After 7.9 hours, when the amount of added TFE reached 12.4 g, the autoclave was cooled, and gas in the system was purged to terminate the reaction. The polymer solution was diluted with HCFC-225cb, and HCFC-141b was added for aggregation. Washing with HCFC-225cb and HCFC-141b was carried out, followed by drying to obtain 25.1 g of polymer F'-1 which is a copolymer of TFE and PSVE. Results are shown in Table 3.

Ex. 4-2 to Ex. 4-4

TFE and PSVE or P2SVE were copolymerized in the same manner as in Ex. 4-1 to obtain polymers F'-2 to F'-4, except that respective conditions were changed as shown in Table 3. Results are shown in Table 3.

TABLE 3

|  | Ex. 4-1 | Ex. 4-2 | Ex. 4-3 | Ex. 4-4 |
|---|---|---|---|---|
| Obtained polymer F | F'-1 | F'-2 | F'-3 | F'-4 |
| Capacity of reactor [mL] | 230 | 230 | 1,000 | 1,000 |
| SO$_2$F group-containing monomer | PSVE | PSVE | P2SVE | P2SVE |
| Amount of SO$_2$F group-containing monomer [g] | 123.8 | 159.0 | 901.7 | 328.0 |
| HCFC-225cb [g] | 35.2 | 0.8 | 0 | 415.5 |
| Polymerization initiator | AIBN | IPP | IPP | V-601 |
| Amount of polymerization initiator [mg] | 63.6 | 47.9 | 90.7 | 223.7 |
| Polymerization temperature [° C.] | 70 | 40 | 40 | 70 |
| Polymerization pressure [MPaG] | 1.14 | 0.46 | 0.55 | 0.69 |
| Polymerization time [hr] | 7.9 | 13.6 | 7.0 | 3.7 |
| Yield of polymer F [g] | 25.1 | 28.1 | 64.8 | 104.1 |

TABLE 3-continued

|  | Ex. 4-1 | Ex. 4-2 | Ex. 4-3 | Ex. 4-4 |
|---|---|---|---|---|
| Ion exchange capacity [meq/g dry resin] | 1.10 | 1.44 | 1.87 | 1.46 |
| Units based on SO$_2$F group-containing monomer [mol %] | 17.7 | 28.5 | 18.3 | 11.8 |
| Units based on SO$_2$F group-containing monomer [mass %] | 48.8 | 63.9 | 58.2 | 45.4 |
| TQ value [° C.] | 225 | 238 | 296 | 241 |
| Tg [° C.] | 8 | 1 | −1 | 7 |

Ex. 5

Ex. 5-1 to Ex. 5-4

The polymers F'-1 to F'-4 were treated to obtain membranes of polymer H'-1 to H'-4 in the same manner as in Ex. 3. Results are shown in Table 4.

TABLE 4

|  | Ex. 5-1 | Ex. 5-2 | Ex. 5-3 | Ex. 5-4 |
|---|---|---|---|---|
| Used polymer F' | F'-1 | F'-2 | F'-3 | F'-4 |
| Obtained polymer H' | H'-1 | H'-2 | H'-3 | H'-4 |
| Used alkaline aqueous solution | Aqueous solution A | Aqueous solution C | Aqueous solution B | Aqueous solution C |
| Softening temperature [° C.] | 99 | 97 | 133 | 138 |
| Elastic modulus at 120° C. [MPa] | 2.70 | 1.81 | 12.5 | 40.8 |
| Conductivity [S/cm] | 0.050 | 0.089 | 0.151 | 0.102 |
| Moisture content [%] | 66 | 89 | 164 | 82 |

It is evident from Tables 1 to 4 that the compound 7-1 has a small molecular weight and has two SO$_2$F groups, whereby even if the proportion of units based on the SO$_2$F group-containing monomer in the polymer F obtained by copolymerization with TFE is made to be lower than that of the conventional polymer F', a polymer H having the ion exchange capacity at the same level can be obtained. The polymer F thereby has a high Tg, and the handling efficiency and the storage stability of the polymer F will improve. The polymer H has a high softening temperature for the same reason. Further, the polymer H has a low moisture content per ion exchange capacity, whereby a membrane of the polymer H which maintains the mechanical strength up to a high temperature can be formed. Further, the amount of expensive SO$_2$F group-containing monomer to be used for the polymer F can be reduced as compared with the conventional polymer F', whereby the membrane of the polymer H can be produced at a low cost. On the other hand, in a case where the proportion of units based on the SO$_2$F group-containing monomer in the polymer F is the same as the conventional polymer F', the ion exchange capacity of the polymer H can be increased, whereby a membrane of the polymer H which has a higher ion conductivity than the conventional polymer H', can be obtained.

Ex. 6

Ex. 6-1

4.3 g of a membrane of the polymer H being cut into small pieces and 75 g of ultrapure water were added in a 100 mL container made of a polytetrafluoroethylene (PTFE), followed by heating at 200° C. for 24 hours. The contents were transferred to a tray made of PTFE and air-dried under nitrogen stream at 30° C. for 64 hours. 200 mL of the dried polymer H-1 was transferred in an autoclave made of glass, and 21.4 g of a mixed solvent of ultrapure water/ethanol (50/50 (mass ratio)) was added thereto. After stirring at 110° C. for 25 hours, 3.87 g of ultrapure water was added for dilution. After stirring at 90° C. for 5 hours, the reaction mixture was left to cool and subjected to filtration by means of a pressure filter (filter paper. PF040, manufactured by Advantec Toyo Kaisha, Ltd.) to obtain 31.9 g of liquid composition S-1 having 13.5 mass % of the polymer H-1 dispersed in the mixed solvent. The viscosity at 25° C. at a shear rate of 76.6 s$^{-1}$ was measured by means of an E-type viscometer, and it was 167 mPa·s.

Ex. 6-2

20.0 g of liquid composition S-3 having 10 mass % of the polymer H-3 dispersed in the mixed solvent was obtained in the same manner as in Ex. 6-1, except that 2.0 g of the polymer H-3, 9.0 g of ethanol and 9.0 g of water were used.

Ex. 7

Ex. 7-1

20 g of a membrane of the polymer H'-1 being cut into small pieces and 56.9 g of a mixed solvent of ethanol/water (60/40 (mass ratio)) were added in an autoclave (internal capacity 200 mL, made of glass), and the autoclave was heated with stirring. After stirring at 115° C. for 16 hours, the autoclave was left to cool, followed by filtration by means of a pressure filter (filter paper. PF040, manufactured by Advantec Toyo Kaisha, Ltd.) to obtain 76.5 g of liquid composition S'-1 having 26.0 mass % of the polymer H'-1 dispersed in the mixed solvent. The viscosity at 25° C. at a shear rate of 76.6 s$^{-1}$ was measured by means of an E-type viscometer, and it was 357 mPa·s.

Ex. 8

Ex. 8-1 and Ex. 8-2

A polymer electrolyte membrane was obtained by using the liquid composition S-1 or the liquid composition S-3 by the following method.

A film was formed by applying the liquid composition on a 100 μm sheet made of an ethylene/tetrafluoroethylene copolymer by means of a die coater, followed by drying at 80° C. for 15 minutes and heat treatment at 185° C. for 30 minutes to obtain a polymer electrolyte membrane made of the polymer H (thickness: 25 μm). Results are shown in Table 5.

Ex. 9

Ex. 9-1

A polymer electrolyte membrane made of the polymer H'-1 (thickness: 25 μm) was obtained in the same manner as in Ex. 8-1, except that the liquid composition S'-1 was used, and the heat treatment was carried out at a temperature of 160° C. for 30 minutes. Results are shown in Table 5.

TABLE 5

| Ex. | Ex. 8-1 | Ex. 8-2 | Ex. 9-1 |
|---|---|---|---|
| Polymer H | H-1 | H-2 | H'-1 |
| Used liquid composition | S-1 | S-3 | S'-1 |
| Softening temperature [° C.] | 151 | 145 | 99 |
| Conductivity [S/cm] | 0.132 | 0.197 | 0.050 |
| Moisture content [%] | 152 | At least 400 | 49 |

Ex. 10

Ex. 10-1

7.25 g of potassium fluoride and 26.6 mL of acetonitrile were charged in a 100 mL four-necked flask provided with a stirrer, a condenser, a thermometer and a dropping funnel. The flask was cooled in an ice bath, and 20.5 g of the reaction liquid obtained in Ex. 1-4 was dropwise added by means of a plastic syringe, while maintaining the internal temperature at from 0 to 10° C. by stirring. Intense heat generation was observed, and 15 minutes was spent for the dropwise addition. After completion of the dropwise addition, the ice bath was changed to a water bath, and the reaction was carried out at from 15 to 20° C. for 1 hour. The flask was cooled in an ice bath again, and 16.0 g of hexafluoropropylene oxide was gas-fed from a 1 L metal container, while maintaining the temperature of the reaction liquid at from 0 to 10° C. After completion of the feeding, the ice bath was changed to a water bath, and the reaction was carried out at from 20 to 25° C. for 48 hours. By-products were removed from the reaction liquid by suction filtration to recover a crude liquid. The solid removed by filtration was washed with an appropriate amount of acetonitrile, and the wash was mixed with the crude liquid. 57.4 g of the crude liquid was quantitatively analyzed by gas chromatography (GC), and it was confirmed that 1.0 mass % of the compound 8b-1 and 4.9 mass % of the compound 8a-1 were contained. The reaction yield of the compound 8b-1 on the compound 5-1 basis was 9.0%, and the reaction yield of the compound 8a-1 was 37.6%.

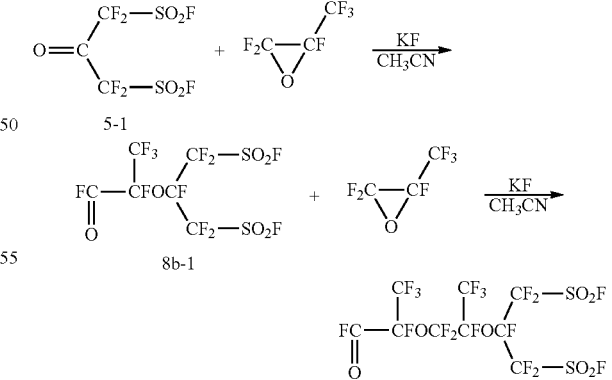

NMR spectrum of compound 8a-1;
$^{19}$F-NMR: −145.5 ppm (—CF$_2$—CF(CF$_3$)—O—, 1F), −138.0 ppm (—O—CF(CF$_2$—SO$_2$F)$_2$, 1F), −131.0 ppm (FOC—CF(CF$_3$)—O—, 1F), −103.1 ppm (—CF$_2$—SO$_2$F, 4F), −82.0 ppm (FOC—CF(CF$_3$)—O—, 3F), −82.0 ppm (—O—CF$_2$—CF(CF$_3$)—, 2F), −80.5 ppm (—CF$_2$—CF(CF$_3$)—O—, 3F), 27.0 ppm (COF, 1F), 46.4 ppm (—SO$_2$F, 2F)

NMR spectrum of compound 8b-1;
$^{19}$F-NMR: −138.0 ppm (—O—CF(CF$_2$—SO$_2$F)$_2$, 1F), −131.0 ppm (FOC—CF(CF$_3$)—O—, 1F), −103.1 ppm (—CF$_2$—SO$_2$F, 4F), −82.0 ppm (FOC—CF(CF$_3$)—O—, 3F), 27.0 ppm (COF, 1F), 46.4 ppm (—SO$_2$F, 2F)

(Ex. 10-2)

A fluidized-bed reactor having a length of 300 mm was produced by using a stainless steel tube having an inner diameter of 11.0 mm. 28 g of glass beads having an average diameter of 150 μm were packed in the fluidized-bed reactor, nitrogen gas was used as fluidization gas, and a metering pump was used to continuously supply starting materials. Outlet gas was collected by means of a trap tube with dry ice and acetone. 4.2 g of the reaction crude liquid in Ex. 10-1 was supplied to the fluidized-bed reactor over 1.5 hours so that the reaction crude liquid in Ex. 10-1/nitrogen gas=5/95 (molar ratio), while maintaining the reaction temperature in the fluidized bed reactor at 325° C. After completion of the reaction, 1.5 g of a crude liquid was obtained from the trap. The crude liquid was quantitatively analyzed by GC, and it was confirmed that 4.1 mass % of the compound 10-1 and 2.6 mass % of the compound 9-1 were contained. The reaction yield of the compound 9-1 on the compound 8a-1 basis was 6.8%, and the reaction yield of the compound 10-1 on the compound 8b-1 basis was 7.2%.

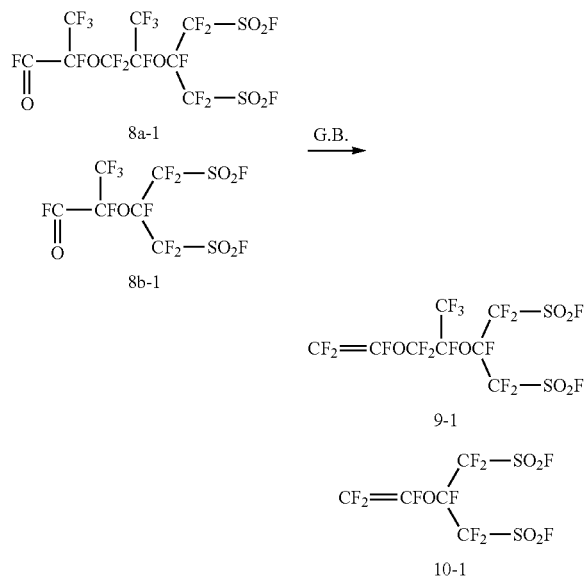

NMR spectrum of compound 9-1;
$^{19}$F-NMR: −145.5 ppm (—CF$_2$—CF(CF$_3$)—O—, 1F), −132.4 ppm (—O—CF(CF$_2$—SO$_2$F)$_2$, 1F), −136.0 ppm (CF$_2$=CF—O—, 1F), −122.0 ppm (CF$_2$=CF—O—, 1F), −114.0 ppm (CF$_2$=CF-0-, 1F), −103.1 ppm (—CF$_2$—SO$_2$F, 4F), −82.0 ppm (—O—CF$_2$—CF(CF$_3$)—, 2F), −80.5 ppm (—CF$_2$—CF(CF$_3$)—O—, 3F), 46.4 ppm (—SO$_2$F, 2F)

NMR spectrum of compound 10-1;
$^{19}$F-NMR: −142.0 ppm (—O—CF(CF$_2$—SO$_2$F)$_2$, 1F), −136.0 ppm (CF$_2$=CF—O—, 1F), −122.0 ppm (CF$_2$=CF—O—, 1F). −114.0 ppm (CF$_2$=CF—O—, 1F), −103.1 ppm (—CF$_2$—SO$_2$F, 4F), 46.4 ppm (—SO$_2$F, 2F)

Ex. 11

80.7 g of the compound 9-1 and 9.1 mg of IPP are added in an autoclave (internal capacity 100 mL, made of stainless steel), followed by cooling and deaeration by liquid nitrogen. The internal temperature is raised to 40° C., and TFE is introduced in the autoclave to maintain the pressure at 0.55 MPaG (gage pressure). TFE is continuously added while maintaining the temperature and the pressure so that the pressure will be constant at 0.55 MPaG. After 7 hours, when the amount of added TFE reaches 2.7 g, the autoclave is cooled to terminate the polymerization, and gas in the system is purged. The reaction liquid is diluted with HFC-52-13p, and HFE-347pc-f is added to aggregate a polymer, followed by filtration. Then, an operation of stirring the polymer in HFC-52-13p and aggregating the polymer with HFE-347pc-f again is repeated twice, followed by drying under reduced pressure at 120° C. overnight to obtain 6.1 g of polymer F-6 which is a copolymer of TFE and the compound 9-1.

The proportion of respective units constituting the polymer F-6 is obtained by $^{19}$F-NMR, whereupon units based on TFE/units based on the compound 9-1=81.7/18.3 (molar ratio). The polymer F-6 has TQ value of 296° C. The polymer F-6 has an ion exchange capacity of 2.0 (meq/g dry resin).

Ex. 12

49.6 g of the compound 9-1 is charged in an autoclave (internal capacity of 100 mL, made of stainless steel) under reduced pressure with cooling with ice water, followed by deaeration, and then 14.9 g of PDD is charged. After raising the temperature to 24° C., 0.1 MPa of nitrogen gas is introduced. After confirming no change in the pressure, 2.10 g of TFE is charged so that the total pressure will be 0.2 MPa (gage pressure). 11.7 mg of PFB dissolved in 0.39 g of HFC-52-13p is added under elevated pressure with nitrogen gas, and then the supply line is washed with 1.5 g of HFC-52-13p. While decreasing the rotational rate of stirring during the reaction from 100 rpm to 50 rpm so that ΔT between the jacket and the internal temperature will be minimum at the internal temperature of 24° C., after 12 hours from the initiation of the polymerization, gas in the system is purged to be replaced with nitrogen. The set temperature of the jacket is set to 24° C., the rotational rate of stirring is set to 5 rpm, and the pressure in the autoclave is gradually reduced to initiate distillation of a mixed liquid of unreacted PDD and the solvent. The set temperature of the jacket is gradually raised to 28° C., and 6.25 g of a distillate is obtained by a cold trap of a mixed liquid of HFC-225cb and dry ice after 2 hours. After stopping the distillation, the contents in the autoclave are diluted with 90 g of HFC-52-13p, followed by stirring at 20 rpm for 16 hours. A polymer solution at 25° C. discharged from the autoclave is added to a mixed liquid of 250 g of HFC-52-13p and 62.5 g of methanol at 20° C. to form particles. After stirring for 30 minutes, 170 g of a part of the polymer particles dispersion is taken out, and 55 g of methanol is added to the polymer particles dispersion. After stirring for 30 minutes, filtration is carried out. Then, washing is carried out by stirring and filtration with a mixed liquid of 50 g of HFC-52-13p and 21 g of methanol. After vacuum drying at 80° C. for 16 hours, vacuum drying at 240° C. is carried out for 16 hours to obtain 13.2 g of the polymer F-7.

The proportion of respective units constituting the polymer F-7 is obtained by $^{19}$F-NMR, and it will be units based on TFE/units based on the compound 9-1/units based on PDD=14.7/18.0/67.3 (molar ratio). The polymer F-7 has TQ value of 272° C. The polymer F-7 has an ion exchange capacity of 1.23 (meq/g dry resin).

Ex. 13

66.0 g of the compound 9-1, 25.9 g of PMVE and 2.03 g of HFC-52-13p are charged in an autoclave (internal capacity of 100 mL, made of stainless steel), followed by cooling and deaeration by liquid nitrogen. After raising the temperature to 40° C., TFE is charged until the pressure reaches 0.80 MPa (gage pressure). After confirming no change in the pressure, from a supply line attached to the autoclave, 0.28 g of a HFC-52-13p solution having 30.86 mg of IPP dissolved therein is added under elevated pressure with nitrogen gas, and then 1.0 g of HFC-52-13p is added to wash the supply line. While maintaining the temperature and the pressure at constant, TFE is continuously supplied to carry out polymerization. After 9.5 hours from the initiation of the polymerization, the autoclave is cooled to terminate the polymerization, and gas in the system is purged to obtain a solution of a polymer. 46.3 g of HFC-52-13p is added to the solution of the polymer and mixed. The temperature of the polymer solution is 25° C. The polymer solution is added to 216.3 g of HFE-347pc-f of −20° C. to aggregate the polymer, and particles are thereby formed. A liquid containing the particles of the polymer is filtered. 62.5 g of HFE-347pc-f is added to the obtained particles of the polymer, followed by stirring and then washing by filtration. The washing operation is carried out twice. The obtained particles of the polymer are dried under reduced pressure at 140° C. for 16 hours to obtain 6.5 g of polymer F-8.

The proportion of the respective units constituting the polymer F-8 is obtained by $^{19}$F-NMR, whereupon units based on TFE/units based on the compound 9-1/units based on PMVE=69.2/13.4/17.4 (molar ratio). The polymer F-8 has TQ value of 255° C. The polymer F-8 has an ion exchange capacity of 1.54 (meq/g dry resin).

INDUSTRIAL APPLICABILITY

The fluorosulfonyl group-containing monomer of the present invention is useful as a starting material for a polymer, etc. to be contained in a catalyst layer or a polymer electrolyte membrane for a membrane/electrode assembly for a polymer electrolyte fuel cell or a membrane/electrode assembly for polymer electrolyte water electrolysis, a cation exchange membrane to be used for alkali chloride electrolysis, water electrolysis or electrodialysis, a diaphragm for a redox flow secondary cell, an ion exchange membrane for an electrochemical hydrogen pump, etc.

The invention claimed is:

1. A fluorosulfonyl group-containing polymer, comprising:
   a plurality of copolymerized units comprising tetrafluoroethylene and a monomer of Formula 9a:

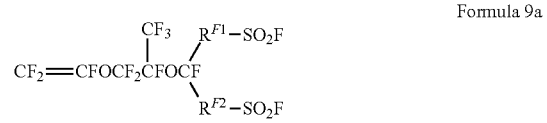

Formula 9a wherein each of $R^{F1}$ and $R^{F2}$ is $C^{F2}$, and
wherein
a content of the copolymerized units of the monomer of Formula 9a is in a range of 13.4 to 18.3 mole %, of the total copolymerized units, and
a volume flow rate TQ of the fluorosulfonyl group-containing polymer is in a range of 200° C. to 330° C.

2. The fluorosulfonyl group-containing polymer of claim 1, further comprising a copolymerized unit selected from the group consisting of chlorotrifluoroethylene, trifluoroethylene, vinylidene fluoride, vinyl fluoride, ethylene, propylene, perfluoro (3-butenyl vinyl ether), a perfluoro (allyl vinyl ether), a perfluoro α-olefin, a (perfluoroalkyl) ethylene, a (perfluoroalkyl) propene, a perfluoro (alkyl vinyl ether) and a perfluoromonomer having a 5-membered ring.

3. A sulfonic acid containing polymer obtained by hydrolysis of the fluorosulfonyl groups of the fluorosulfonyl group-containing polymer of claim 1; wherein an ion exchange capacity of the sulfonic acid containing polymer is from 0.5 to 2.5 meq/g dry resin.

4. A sulfonic acid containing polymer obtained by hydrolysis of the fluorosulfonyl groups of the fluorosulfonyl group-containing polymer of claim 2; wherein an ion exchange capacity of the sulfonic acid containing polymer is from 0.5 to 2.5 meq/g dry resin.

* * * * *